(12) United States Patent
Petersen

(10) Patent No.: US 10,245,044 B2
(45) Date of Patent: *Apr. 2, 2019

(54) SURGICAL DEVICES AND METHODS FOR IMMOBILIZING A SACROILIAL JOINT

(71) Applicant: David Petersen, Clearwater, FL (US)

(72) Inventor: David Petersen, Clearwater, FL (US)

( * ) Notice: Subject to any disclaimer, the term of this patent is extended or adjusted under 35 U.S.C. 154(b) by 47 days.

This patent is subject to a terminal disclaimer.

(21) Appl. No.: 15/006,747

(22) Filed: Jan. 26, 2016

(65) Prior Publication Data

US 2017/0209155 A1    Jul. 27, 2017

(51) Int. Cl.

| | | |
|---|---|---|
| *A61B 17/58* | (2006.01) | |
| *A61B 17/16* | (2006.01) | |
| *A61F 2/30* | (2006.01) | |
| *A61F 2/46* | (2006.01) | |
| *A61B 17/02* | (2006.01) | |
| *A61B 17/17* | (2006.01) | |

(52) U.S. Cl.
CPC ........ *A61B 17/1635* (2013.01); *A61B 17/025* (2013.01); *A61B 17/1671* (2013.01); *A61B 17/1757* (2013.01); *A61F 2/30988* (2013.01); *A61F 2/4601* (2013.01); *A61B 2017/0256* (2013.01); *A61F 2002/30622* (2013.01); *A61F 2002/30995* (2013.01)

(58) Field of Classification Search
CPC ........ A61F 2002/30995; A61F 2/30988; A61F 2002/30622; A61F 2/4603; A61B 17/1635; A61B 17/1671; A61B 17/1757; A61B 17/025; A61B 17/0256; A61B 17/17; A61B 17/1742

USPC ...... 623/17.11–17.16; 606/246–279, 99–100
See application file for complete search history.

(56) References Cited

U.S. PATENT DOCUMENTS

| | | | | |
|---|---|---|---|---|
| 8,808,377 | B2 * | 8/2014 | Donner | A61F 2/30988 623/17.11 |
| 8,986,348 | B2 * | 3/2015 | Reiley | A61B 17/1659 606/279 |
| 2011/0087294 | A1 * | 4/2011 | Reiley | A61B 17/1659 606/279 |
| 2011/0125268 | A1 * | 5/2011 | Reiley | A61B 17/1615 623/17.11 |
| 2011/0264229 | A1 * | 10/2011 | Donner | A61F 2/30988 623/18.11 |

(Continued)

*Primary Examiner* — Zade Coley
*Assistant Examiner* — Jessica Weiss
(74) *Attorney, Agent, or Firm* — Allen F. Bennett; Bennett Intellectual Property

(57) ABSTRACT

The present invention includes tools, tool kits and methods useful for treating an SI joint. In one embodiment, the present invention is a method including the steps of: implanting a graft into a SI joint of a patient, wherein the implanting comprises: creating an incision in the patient's skin proximal to the patient's SI joint; dilating the incision; creating a void in the SI joint, wherein the creating comprises displacing a portion of the patient's ilium and a portion of the patient's sacrum; and inserting a graft into the void in the SI joint, wherein the graft contacts the patient's iluim and the patient's sacrum and wherein the graft is configured to substantially fuse the patient's ilium to the patient's sacrum, thereby substantially immobilizing the patient's SI joint; inserting and immobilizing screw perpendicular to and through the inserts within the void created in the sacroiliac joint.

9 Claims, 35 Drawing Sheets

(56) References Cited

U.S. PATENT DOCUMENTS

2013/0267836 A1* 10/2013 Mauldin .................. A61B 6/12
600/424

* cited by examiner

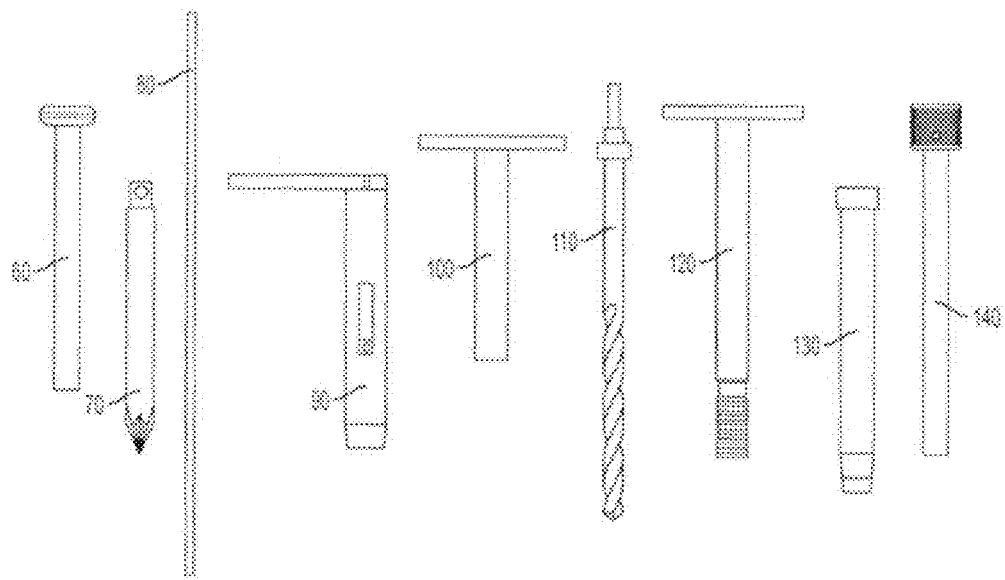
FIG. 3
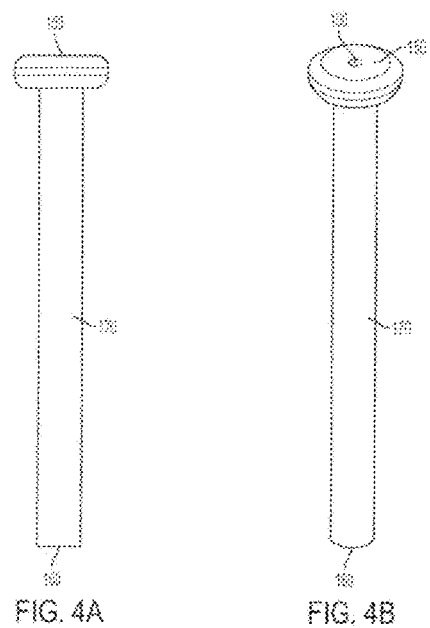 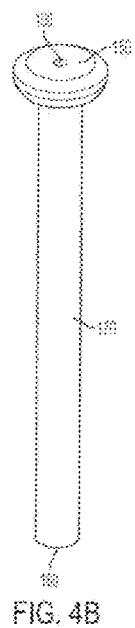 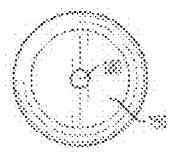
FIG. 4C
FIG. 4A      FIG. 4B
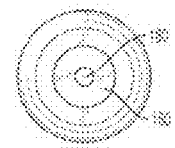
FIG. 4D

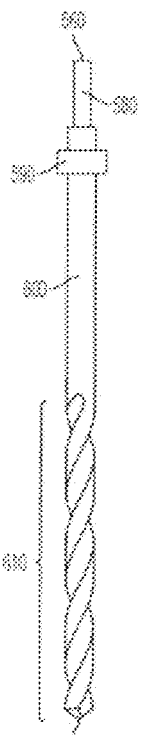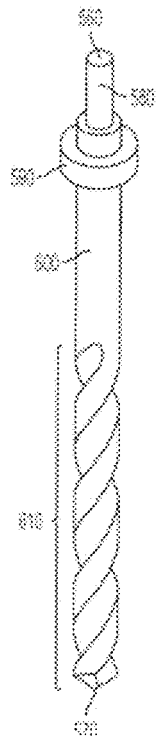
FIG. 9A  FIG. 9B
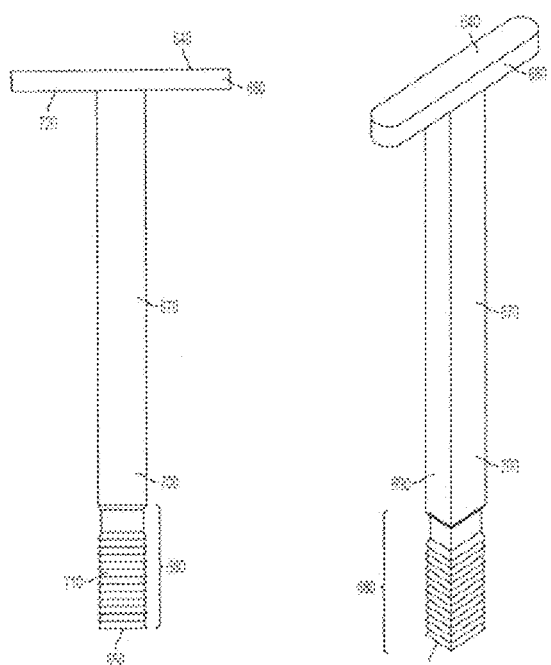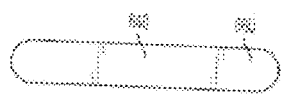
FIG. 10C
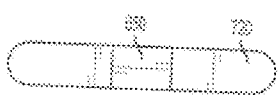
FIG. 10D
FIG. 10A  FIG. 10B

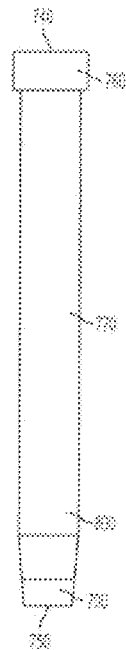 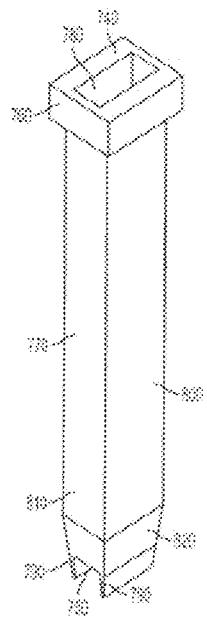 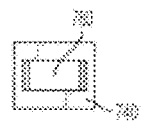 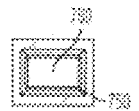
FIG. 11A   FIG. 11B   FIG. 11C
FIG. 11D
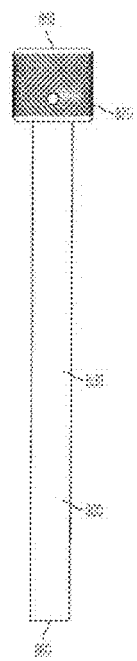 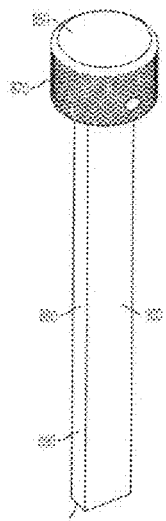 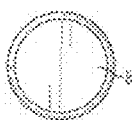 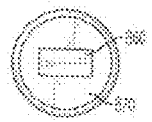 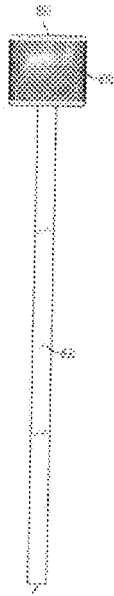
FIG. 12A   FIG. 12B   FIG. 12C   FIG. 12D   FIG. 12E

ALL DIMENSIONS ARE IN MILLIMETERS

ALL DIMENSIONS ARE IN MILLIMETERS

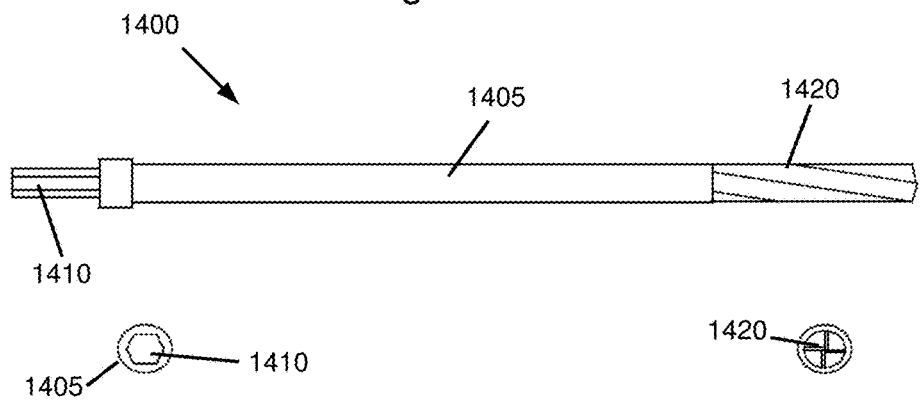
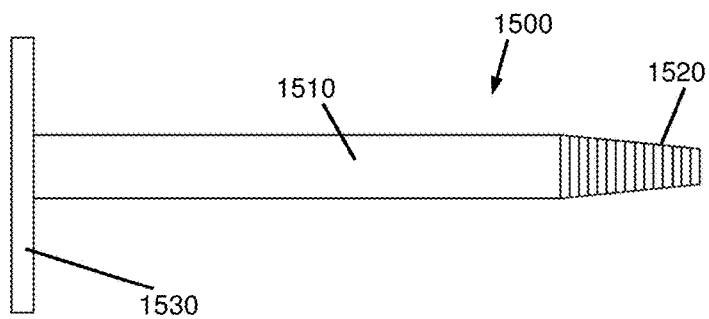
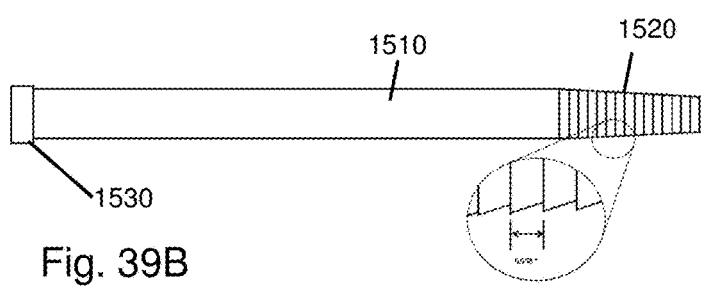
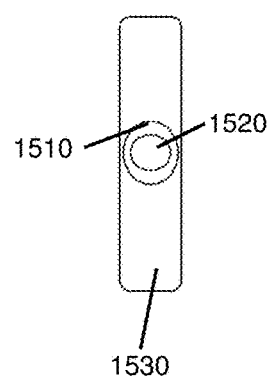

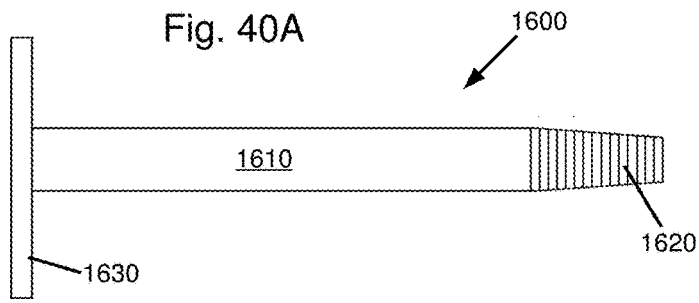
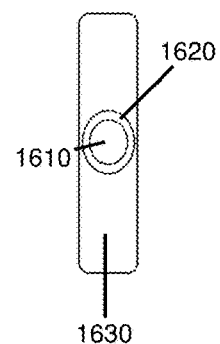
Fig. 40A
Fig. 40C
Fig. 40B
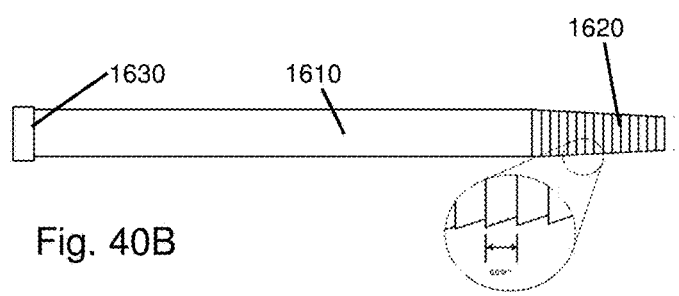
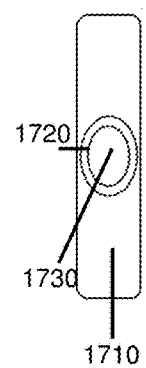
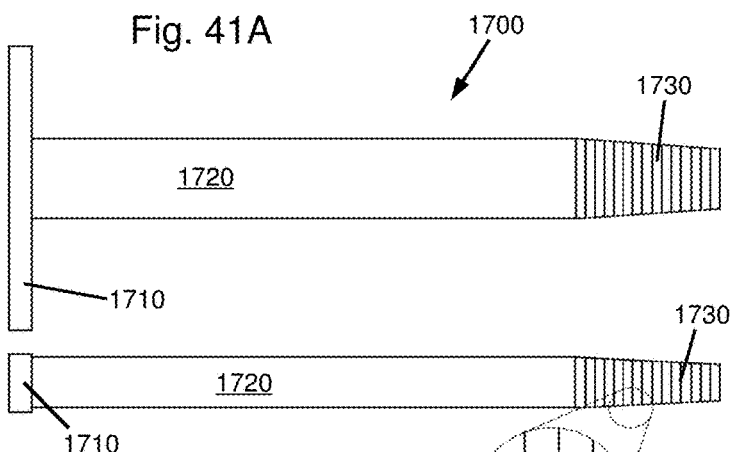
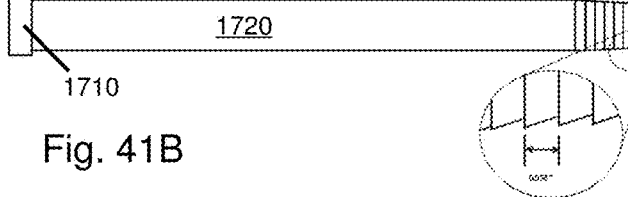
Fig. 41A
Fig. 41C
Fig. 41B

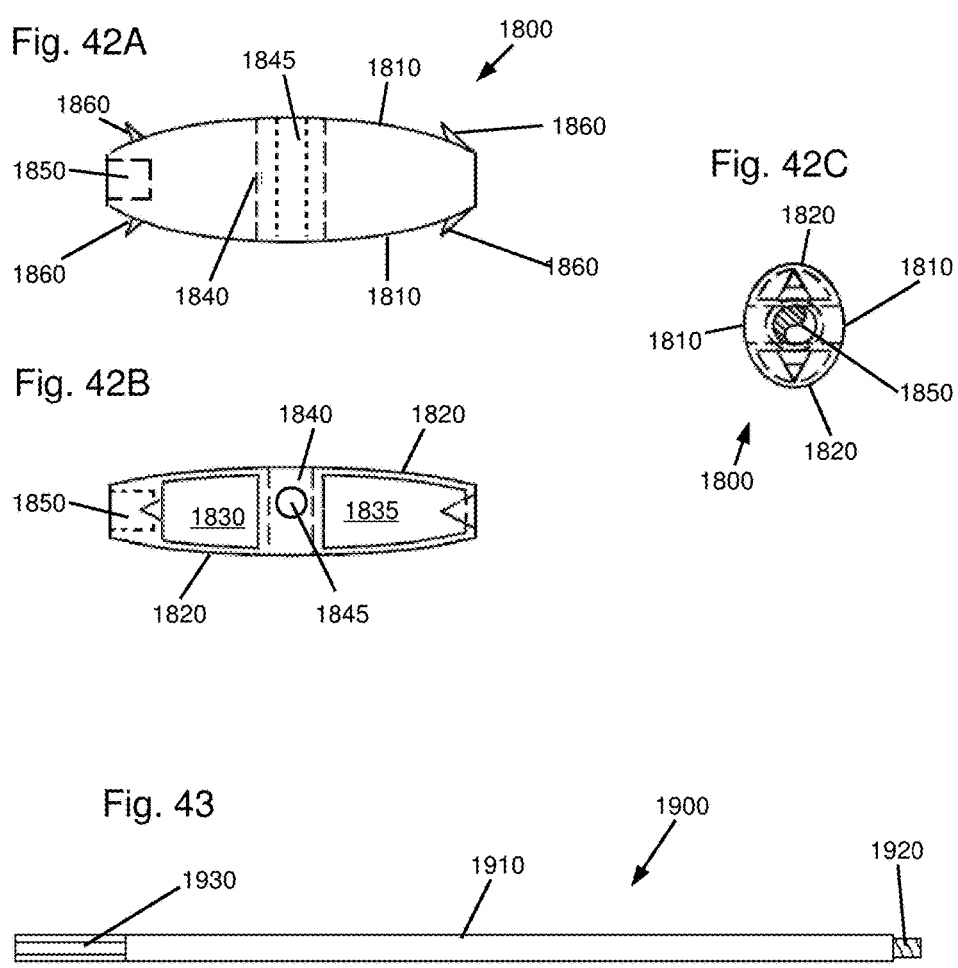

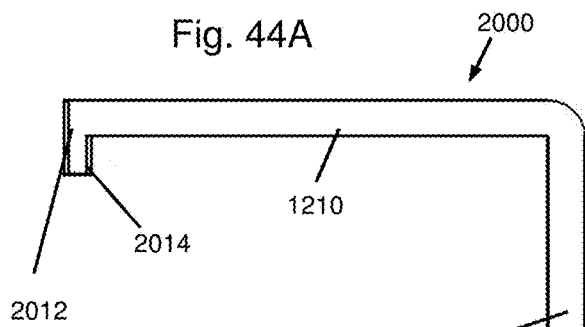
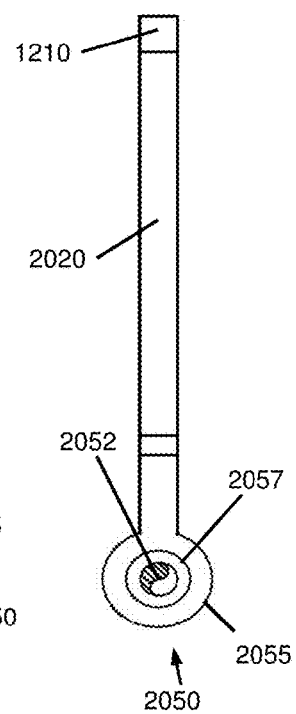
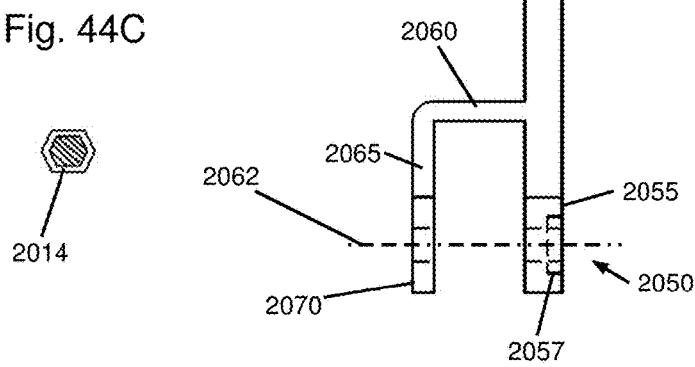
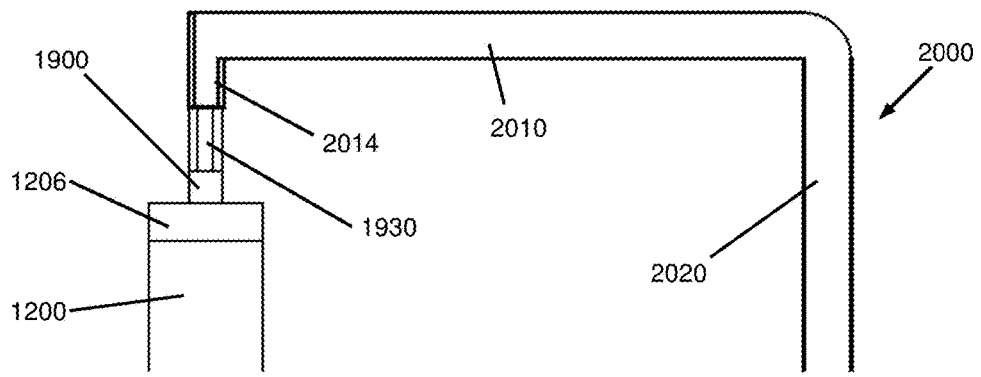

SURGICAL DEVICES AND METHODS FOR IMMOBILIZING A SACROILIAL JOINT

CROSS-REFERENCE TO RELATED APPLICATIONS

This application is a Continuation-in-Part of U.S. Pat. No. 9,241,798 filed on Mar. 19, 2010 and claims the benefit, under 35 U.S.C. § 119, of provisional U.S. Application Ser. No. 61/162,103, filed Mar. 20, 2009, the entire contents and substance of which is hereby incorporated by reference.

STATEMENT REGARDING FEDERALLY SPONSORED RESEARCH OR DEVELOPMENT

Not Applicable.

NAMES OF PARTIES TO A JOINT RESEARCH AGREEMENT

Not Applicable

REFERENCE TO SEQUENCE LISTING, A TABLE, OR A COMPUTER PROGRAM LISTING APPENDIX SUBMITTED ON A COMPACT DISC AND INCORPORATION-BY-REFERENCE OF THE MATERIAL

Not Applicable.

COPYRIGHT NOTICE

Not Applicable

BACKGROUND OF THE INVENTION

Field of the Invention

The present invention relates generally to medical devices and medical methods. More particularly, the present invention relates to surgical methods, surgical tools, and surgical tool kits useful for treatment of the sacroiliac joint.

Description of the Related Art

In the United States, about 10% of the population will suffer from back pain sometime in the next year. This occurrence is more than any other injury or disease except for the common cold and flu. About one-third of those suffering from back pain will not recover and will live with persistent, disabling symptoms. These numbers are cumulative year after year.

One cause of pain in the back and lower extremities is caused by an injury or some other damage to the sacroiliac joint ("SI joint"). The SI joint is a firm, small joint that lies at the junction of the spine and the pelvis and it plays a major role in transferring the load of a person's upper body to the lower body. A person has two SI Joints one on the right side of the pelvis and the other on the left side. FIG. 1 illustrates a model of an SI joint, showing the SI joint 30 located between the sacrum 10 and the ilium 30. The SI joint, like other joints, is lined with cartilage and other connective tissue to prevent bone on bone contact between the sacrum and the ilium. This cartilage may become damage or degraded (e.g., because of osteoarthritis). Without the spongy cartilaginous cushion, joint bones begin to rub against each other when at rest and during movement causing a substantial amount of pain. Therefore, one option to treat this type of pain is to join rubbing portions of bone together so that this painful friction does not occur.

Various methods for treating SI joint exist, but are not widely used. For example, FIG. 2 shows a method wherein screws 50 are surgically installed through ilium 20, across the SI joint 30, and into the sacrum 10. Other existing methods include installation of a metal plate to stabilize the SI joint. Most of these methods have substantial risks, result in substantial discomfort to the patient, require an open, invasive surgical procedure that requires a long recovery time and/or has a low success rate in eliminating or reducing pain resulting from SI joint problems.

BRIEF SUMMARY OF THE INVENTION

The present invention includes surgical tools, tool kits, and surgical methods useful for the treatment of a patient's SI joint.

In some embodiments, the present invention is a method useful for treating a patient's SI joint. In some embodiments, the present invention is a method including the steps of implanting a graft into a SI joint of a patient, wherein the implanting includes: creating an incision in the patient's skin proximal to the patient's SI joint; creating a void in the SI joint, wherein the creating comprises displacing a portion of the patient's ilium and a portion of the patient's sacrum; inserting a graft into the void in the SI joint, wherein the graft contacts the patient's iluim and the patient's sacrum and wherein the graft is configured to substantially fuse the patient's ilium to the patient's sacrum, thereby substantially immobilizing the patient's SI joint. In some such embodiments, the creating an incision comprises inserting a pin into the patient. In some embodiments the method also includes the step of dilating the incision. In some embodiments the dilating the incision includes inserting a dilator over the pin and into the incision. In other embodiments the creating a void includes: inserting a guide over the dilator and into the incision; securing the guide in the incision, removing the dilator; inserting a drill guide into the guide; inserting a drill bit into the drill guide; and drilling the void in the SI joint; and removing the drill bit and the drill guide from the guide; inserting a broach into the guide, wherein the broach has a proximal and a distal end, wherein the proximal end is configured to enlarge the void. In further embodiments the proximal end of the broach is configured to enlarge the void to a size and shape approximately the size and shape of the graft. In yet further embodiments the securing the guide in the incision comprises inserting a pin through a portion of the guide and into the patient. In some embodiments the drill guide is inserted into the guide until a stop on the drill guide contacts a distal surface of the guide. In yet other embodiments the drill bit is inserted into the drill guide until a stop on the drill bit contacts a distal surface of the drill guide. In other embodiments the broach is inserted into the guide until a stop on the broach contacts a distal surface of the guide. In some embodiments the inserting the graft includes: attaching the graft to an inserter, wherein the inserter has a proximal end and a distal end, wherein the proximal end is configured to attach to the graft, and wherein the inserter comprises a channel running from its distal end to its proximal end; inserting the inserter into the guide until a stop on the inserter contacts a distal surface of the guide; inserting an impactor having a proximal and a distal end into the channel in the inserter until the impactor contacts the graft in a manner that separates the graft from the inserter and places the graft in the void. In further embodiments the graft is substantially rectangular and has a proximal end and a distal end, wherein the graft is tapered from the proximal end to the distal end. In some embodiments the graft is tapered with a Morris taper.

In other embodiments the present invention includes a method including the steps of: implanting a graft into a SI joint of a patient, wherein the implanting includes: creating an incision in the patient's skin proximal to the patient's SI joint, wherein the creating an incision comprises inserting a pin into the patient; dilating the incision, wherein the dilating the incision comprises inserting a dilator over the pin and into the incision; creating a void in the SI joint, wherein the creating comprises displacing a portion of the patient's ilium and a portion of the patient's sacrum by: inserting a guide over the dilator and into the incision; securing the guide in the incision, removing the dilator; inserting a drill guide into the guide; inserting a drill bit into the drill guide; and drilling the void in the SI joint; and removing the drill bit and the drill guide from the guide; inserting a broach into the guide, wherein the broach has a proximal and a distal end, wherein the proximal end is configured to enlarge the void; inserting a graft into the void in the SI joint, wherein the graft contacts the patient's iluim and the patient's sacrum and wherein the graft is configured to substantially fuse the patient's ilium to the patient's sacrum, thereby substantially immobilizing the patient's SI joint, wherein the inserting the graft comprises: attaching the graft to an inserter, wherein the inserter has a proximal end and a distal end, wherein the proximal end is configured to attach to the graft, and wherein the inserter comprises a channel running from its distal end to its proximal end; inserting the inserter into the guide until a stop on the inserter contacts a distal surface of the guide; inserting an impactor having a proximal and a distal end into the channel in the inserter until the impactor contacts the graft in a manner that separates the graft from the inserter and places the graft in the void. In other embodiments the present invention is surgical tools such as those described herein.

In some embodiments the present invention is a surgical tool kit. In some embodiments the tool kit includes one or more of a pin, a dilator, a dilator impactor, a guide, a drill guide, a drill bit, a broach, an inserter, an impactor and a graft. In some embodiments the kit comes in an autoclavable tool kit box.

These and other objects and advantages of the present invention will become apparent from a reading of the attached specification and appended claims. There has thus been outlined, rather broadly, the more important features of the invention in order that the detailed description thereof that follows may be better understood, and in order that the present contribution to the art may be better appreciated. There are features of the invention that will be described hereinafter and which will form the subject matter of the claims appended hereto.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3 is a perspective view of embodiments of tools in accordance with the present invention.

FIG. 4A is a side elevation view of a dilator impactor in accordance with the principles of the invention.

FIG. 4B is a perspective view of a dilator impactor in accordance with the principles of the invention.

FIG. 4C is a top plan view of a dilator impactor in accordance with the principles of the invention.

FIG. 4D is a bottom plan view of a dilator in accordance with the principles of the invention.

FIG. 9A is a side elevation view of a drill bit in accordance with the principles of the invention.

FIG. 9B is a perspective view of a drill bit in accordance with the principles of the invention.

FIG. 10A is a side elevation view of a broach in accordance with the principles of the invention.

FIG. 10B is a perspective view of a broach in accordance with the principles of the invention.

FIG. 10C is a top plan view of a broach in accordance with the principles of the invention.

FIG. 10D is a bottom plan view of a broach in accordance with the principles of the invention.

FIG. 11A is a side elevation view of an inserter in accordance with the principles of the invention.

FIG. 11B is a perspective view of an inserter in accordance with the principles of the invention.

FIG. 11C is a top plan view of an inserter in accordance with the principles of the invention.

FIG. 11D is a bottom plan view of an inserter in accordance with the principles of the invention.

FIG. 12A is a front elevation view of an impactor in accordance with the principles of the invention.

FIG. 12B is a perspective view of an impactor in accordance with the principles of the invention.

FIG. 12C is a top plan view of an impactor in accordance with the principles of the invention.

FIG. 12D is a bottom plan view of an impactor in accordance with the principles of the invention.

FIG. 12E is another side elevation view of an impactor in accordance with the principles of the invention.

FIG. 22C is a perspective view of an inserter and a guide in accordance with the principles of the invention.

FIG. 38A is a side elevation view of a drill bit in accordance with the principles of the invention;

FIG. 38B is a top plan view of a drill bit in accordance with the principles of the invention;

FIG. 38C is a bottom plan view of a drill bit in accordance with the principles of the invention;

FIG. 39A is a side elevation view of a small broach in accordance with the principles of the invention;

FIG. 39B is another side elevation view of a small broach in accordance with the principles of the invention;

FIG. 39C is a top plan view of a small broach in accordance with the principles of the invention;

FIG. 40A is a side elevation view of a medium broach in accordance with the principles of the invention;

FIG. 40B is another side elevation view of a medium broach in accordance with the principles of the invention;

FIG. 40C is a top plan view of a medium broach in accordance with the principles of the invention;

FIG. 41A is a side elevation view of a large broach in accordance with the principles of the invention;

FIG. 41B is another side elevation view of a large broach in accordance with the principles of the invention;

FIG. 41C is a top plan view of a large broach in accordance with the principles of the invention;

FIG. 42A is a side elevation view of an insert in accordance with the principles of the invention;

FIG. 42B is another side elevation view of an insert in accordance with the principles of the invention;

FIG. 42C is a bottom plan view of an insert in accordance with the principles of the invention;

FIG. 43 is a side elevation view of an inserter in accordance with the principles of the invention;

FIG. 44A is a side elevation view of a screw alignment guide in accordance with the principles of the invention;

FIG. 44B is another side elevation view of a screw alignment guide in accordance with the principles of the invention;

FIG. 44C is a bottom plan view of a portion of a screw alignment guide in accordance with the principles of the invention;

FIG. 45 is a side elevation view of a portal, inserter and screw alignment guide in accordance with the principles of the invention;

FIG. 46A is a side elevation view of a screw sleeve in accordance with the principles of the invention;

FIG. 46B is another side elevation view of a screw sleeve in accordance with the principles of the invention;

FIG. 46C is a top plan view of a screw sleeve in accordance with the principles of the invention;

FIG. 47A is a side elevation view of a drill guide in accordance with the principles of the invention;

FIG. 47B is another side elevation view of a drill guide in accordance with the principles of the invention;

FIG. 47C is a top plan view of a drill guide in accordance with the principles of the invention;

FIG. 48A is a side elevation view of a pin guide in accordance with the principles of the invention;

FIG. 48B is another side elevation view of a pin guide in accordance with the principles of the invention;

FIG. 48C is a top plan view of a pin guide in accordance with the principles of the invention;

FIG. 49 is a side elevation view of a screw alignment guide, a screw sleeve, a drill guide and a pin guide engaged with one another in accordance with the principles of the invention;

Figure 50:
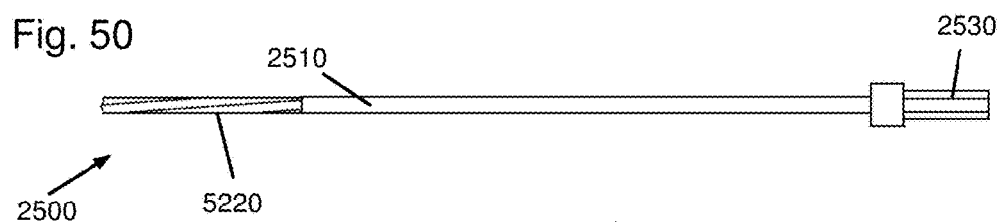
Figure 51:
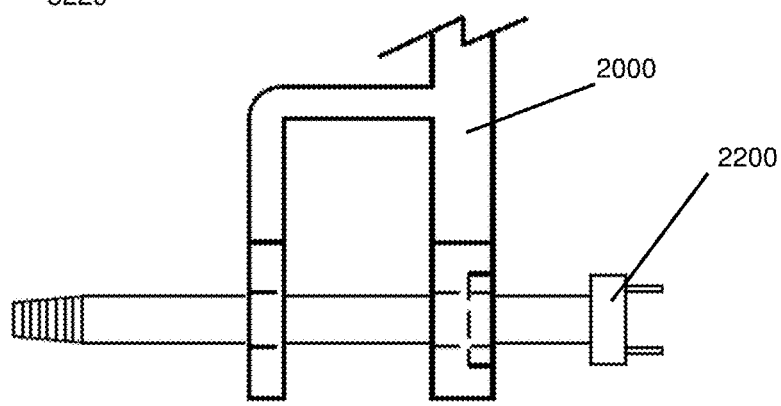
Figure 52A:
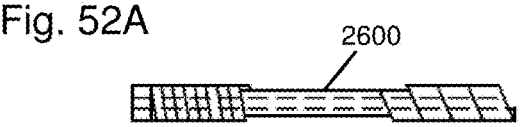
Figure 52B:

FIG. 50 is a side elevation view of a drill bit in accordance with the principles of the invention;

FIG. 51 is a side elevation view of a screw alignment guide and a screw sleeve in accordance with the principles of the invention;

FIG. 52A is a side cross-sectional view of a screw in accordance with the principles of the invention;

FIG. 52B is a bottom plan view of a screw in accordance with the principles of the invention.

DETAILED DESCRIPTION

In the following paragraphs, the present invention will be described in detail by way of example with reference to the attached figures. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

The present invention relates to treatment of a patient's SI joint. In preferred embodiments, the present invention relates to a minimally invasive procedure for fusing one or both of a patient's SI joints. In some embodiments, the procedure may be performed as an out-patient procedure with minimal recovery time. The present invention relates to tools, tool kits and procedures for treating a patient's SI joint.

In some embodiments the present invention is a tool, tools or a tool kit that may be used in a surgical method for treating a patient's SI joint.

Instruments of the Present Invention:

In some embodiments the present invention is a tool, tools or a tool kit that may be used in a surgical method for treating a patient's SI joint. Exemplary tools are described herein. With reference to FIG. 3, various tools are depicted including, dilator 70, dilator impactor 60, pin 80, guide 90, drill guide 100, drill bit 110, broach 120, inserter 130, and impactor 140. These tools may be made of any suitable material, including medical grade plastics, metals, or alloys. In some embodiments the tools are single use, in other embodiments the tools may be reused (and autoclaved, cleaned or otherwise suitably disinfected for further use). The tools may have various configurations, including those that differ from those depicted and specifically described herein. In specific embodiments, the tools are configured to interact with the other tools in a manner that aids the surgeon in keeping a proper orientation for accessing and within the patient's SI joint. Embodiments of these tools are described in greater detail in this section and in the description of the methods of the present invention. Notably, tools other than those described herein may be used in the methods of the present invention.

FIGS. 4A-E illustrate an embodiment of a dilator impactor 60. The dilator impactor 60 may be any structure suitable to apply force or transmit force from a source to an instrument or device capable of dilating an incision made in a human or other animal, such as dilator 70 (FIG. 5A-E). Dilator impactor 60 may have any suitable configuration and dimensions and may be made of any suitable material. Suitable materials are generally those that are substantially rigid such that they transfer force rather than absorb force (e.g., rigid metals, alloys). In the depicted embodiment, dilator impactor 60 has a distal end 150 (the references distal and proximal in this context are in relation to the patient—i.e., a distal end is farther away from a patient), a proximal end 160, a body 170 and a channel 180.

Distal end 150 of dilator impactor 60 is configured to receive force from an outside source. In some embodiments, distal end 150 may have a substantially flattened surface (e.g., as depicted in FIGS. 4A-C) to provide a suitable surface area that may be contacted with a hammer or similar instrument, or to facilitate the application of force by an operator (e.g., a surgeon) of the dilator impactor 60. Body 170 may have any suitable configuration and dimensions. In the depicted embodiment, body 170 is cylindrical, but it may also be, for example, oval, square, rectangular, triangular, or any other suitable shape or configuration. Proximal end 160 may have any suitable configuration that permits the transfer of force to an instrument or device capable of dilating an incision made in a human or other animal. In some embodiments, proximal end 160 is substantially flat. In some embodiments dilator impactor 60 has a channel 180 that runs from distal end 150 to proximal end 160. Channel 180 may have any suitable dimensions and configurations. In some embodiments, channel 180 facilitates alignment of dilator impactor 60 with the dilation device or structure. In some embodiments, channel 180 is configured to accommodate a pin 80 (FIGS. 6A-B) as described herein or a guide wire or any structure providing guidance to the tools.

FIGS. 5A-F illustrate an embodiment of a dilator 70. Dilator 70 may be any device or structure capable of dilating an incision made in a human or other animal. Dilator 70 may be made of any suitable material and may have any suitable dimensions and configuration. In the depicted embodiments, dilator 70 has a distal end 200, a proximal end 210, a body 220, a removal structure 230, a tapered region 240, and a channel 250. Distal end 200 may have any suitable configuration and in some embodiments is configured to interact with a dilator impactor 60 in a manner that permits reasonably efficient transfer of force from dilator impactor 60 to dilator 70. Proximal end 210 may have any configuration suitable to dilate an opening or incision, for example an incision made by a pin 80, in a human's flesh and dilate that incision to increase its size. In some embodiments, tapered region 240 includes distal end 210, such that body 220 becomes narrower in the tapered region 240 and is at its narrowest at distal end 210. In some embodiments, distal end 210 is configured to enter an incision made by a pin 80. In some embodiments, distal end 210 and tapered region 240 are configured to permit distal end 210 to penetrate down to a patient's SI joint (e.g., as in FIG. 14A).

Body 220 of dilator 70 may have any suitable configuration, dimensions and may be made of any suitable material. In some such embodiments, body 220 is configured to interact with guide 90 (FIGS. 7A-F) such that it may fit suitably within channel 380 of guide 90. In some such embodiments, body 220 is configured so that it may enter channel 380 of guide 90 in a manner that insures that guide 90 is properly oriented with SI joint 30. In some such embodiments body 220 is rectangular having a first surface 260 which has a width that is greater than a second surface 270. Channel 250 may have any suitable dimensions and configurations, and it runs from distal end 200 to proximal end 210. In some embodiments, channel 250 facilitates alignment of dilator 70 with an incision 940 made in the patient 950 (see FIG. 14C). Channel 250 can also facilitate alignment of dilator impactor 60 with dilator 70. In some embodiments, channel 250 is configured to accommodate a pin 80 (FIGS. 6A-B) as described herein or a guide wire.

Dilator 70 may have any suitable dimensions. The dimensions of an embodiment of dilator 70 are presented in FIG. 27, which shows a length from distal end 200 to proximal end 210 of about 179.6 mm, a width on first surface 260 of about 13.5 mm, a width of second surface 270 of about 11.5 mm, and a radius of removal structure 230 of about 3.5 mm. In other embodiments, dilator 70 may have a width of about 130 mm to about 230 mm, of about 150 mm to about 200 mm, or about 170 mm to about 190 mm. In other embodiments, dilator 70 may have a width of first surface 260 of about 8 mm to about 19 mm, of about 10 to about 15 mm, or of about 12 mm to about 14 mm. In other embodiments, dilator 70 may have a width of second surface 270 of about 6 mm to about 15 mm, of about 8 mm to about 12 mm, or of about 9 mm to about 11 mm. In some embodiments, removal structure 230 has a radius of about 2 mm to about 5 mm. In other embodiments, removal structure 230 may have a different configuration and any suitable dimensions. In some embodiments, first surface 260 and second surface 270 have widths that are equal.

Figure 1:
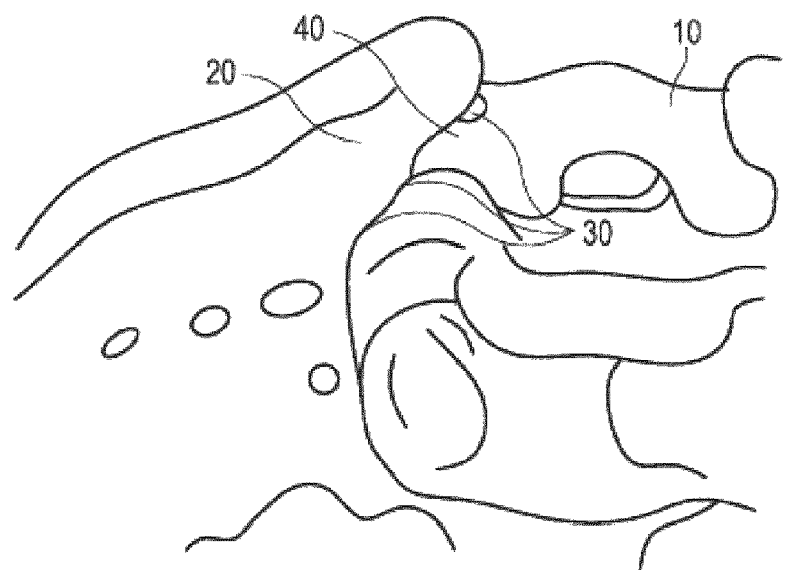
FIG. 1 is a perspective view of an SI joint and the surrounding bones.
Figure 2:
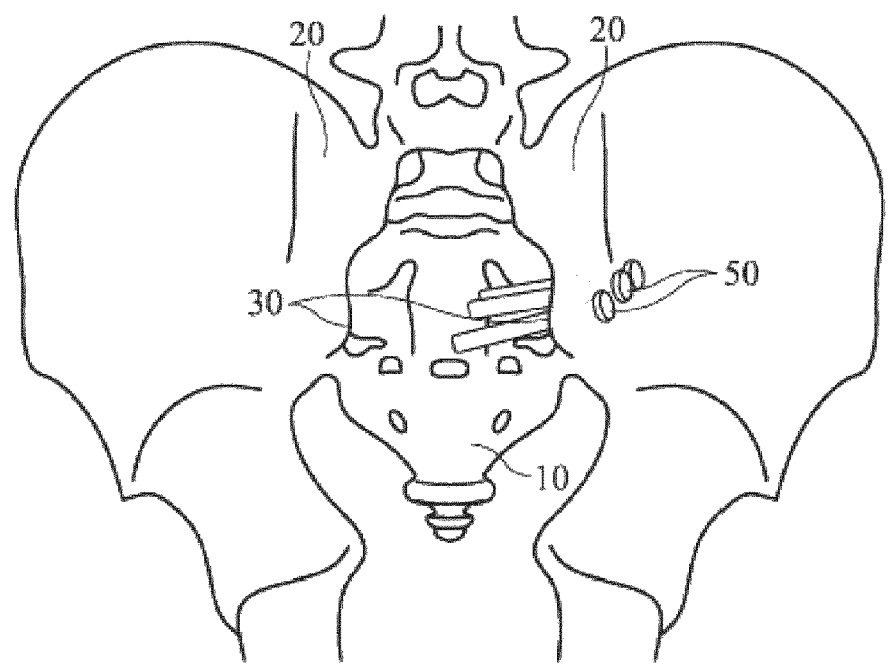
FIG. 2 is a prior art SI joint treatment.
Figure 5A:
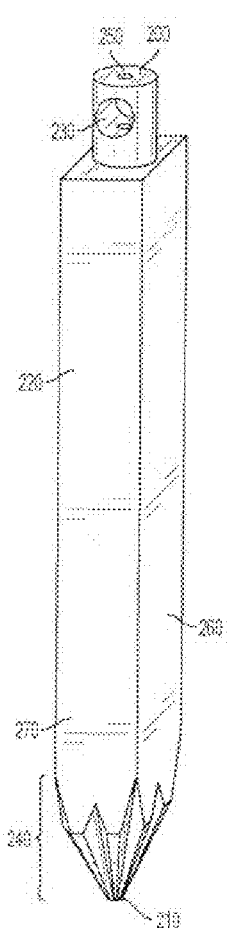
FIG. 5A is a perspective view of a dilator in accordance with the principles of the invention.
Figure 5B:
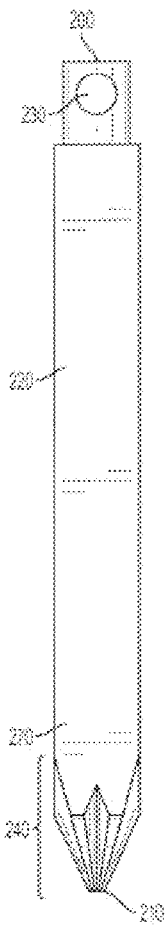
FIG. 5B is a side elevation view of a dilator in accordance with the principles of the invention.
Figure 5C:
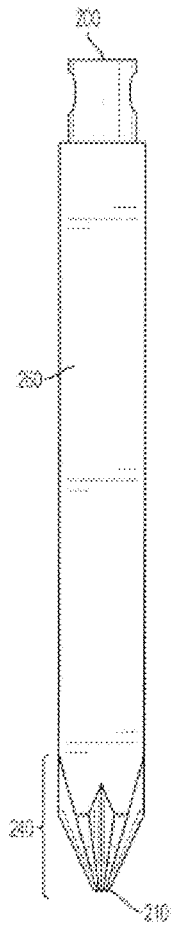
FIG. 5C is another side elevation view of a dilator in accordance with the principles of the invention.
Figure 5D:
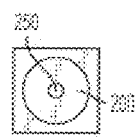
FIG. 5D is a top view of a dilator in accordance with the principles of the invention.
Figure 5E:
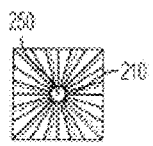
FIG. 5E is a bottom view of a dilator in accordance with the principles of the invention.
Figures 6A, 6B:
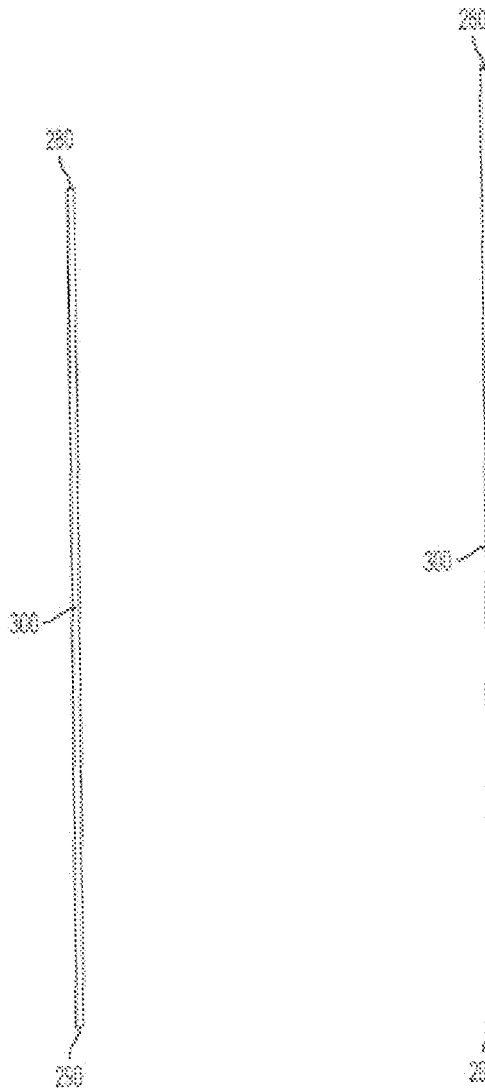
FIG. 6A is a side view of a pin in accordance with the present invention.
FIG. 6B is another side view of a pin in accordance with the principles of the invention.
Figure 7A:
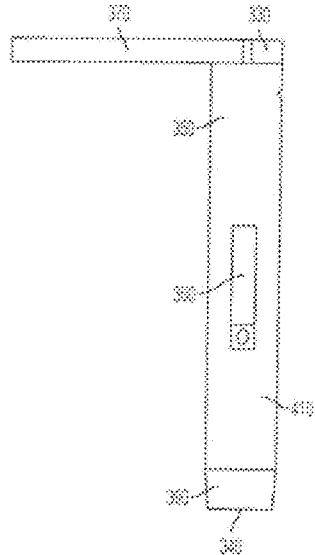
FIG. 7A is a side elevation view of a guide in accordance with the principles of the invention.
Figure 7B:
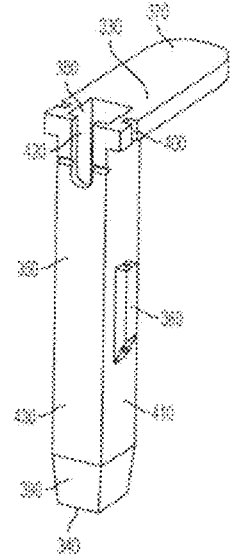
FIG. 7B is a perspective view of a guide in accordance with the principles of the invention.
Figure 7C:
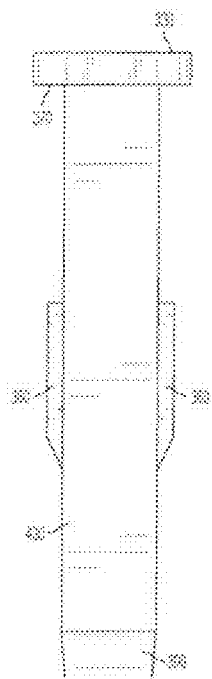
FIG. 7C is a front elevation view of a guide in accordance with the principles of the invention.
Figure 7D:
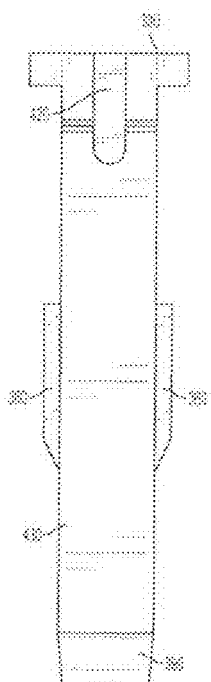
FIG. 7D is a back elevation view of a guide in accordance with the principles of the invention.
Figure 7E:
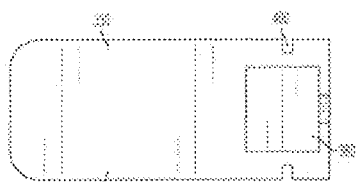
FIG. 7E is a top plan view of a guide in accordance with the principles of the invention.
Figure 7F:
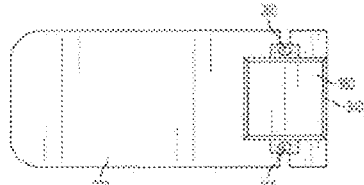
FIG. 7F is a bottom plan view of a guide in accordance with the principles of the invention.
Figure 8A:
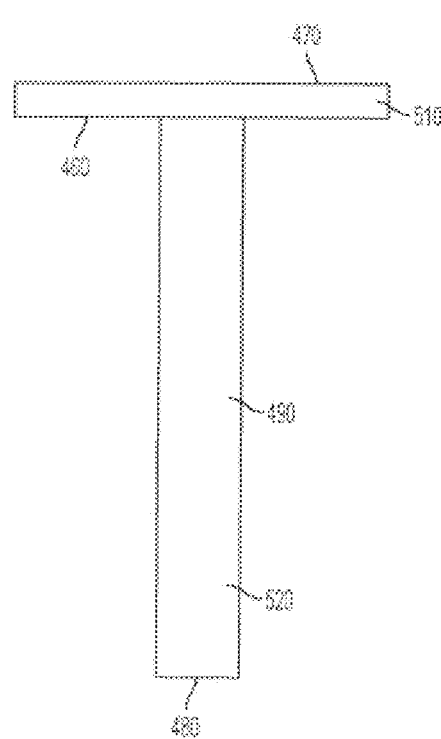
FIG. 8A is a side elevation view of a drill guide in accordance with the principles of the invention.
Figure 8B:
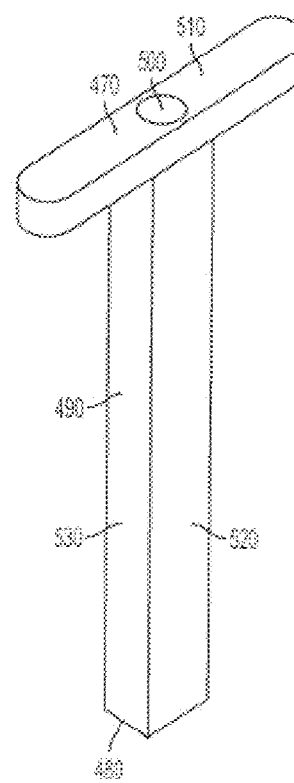
FIG. 8B is a perspective view of a drill guide in accordance with the principles of the invention.
Figure 8C:
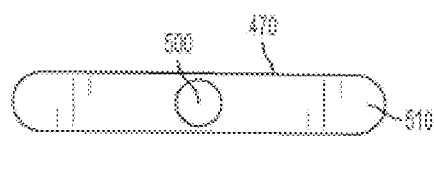
FIG. 8C is a top plan view of a drill guide in accordance with the principles of the invention.
Figure 8D:
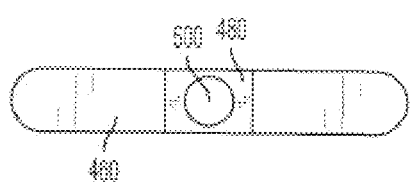
FIG. 8D is a bottom plan view of a drill guide in accordance with the principles of the invention.

FIGS. 6A and 6B illustrate an embodiment of pin 80. In the depicted embodiments, pin 80 has distal end 280, proximal end 290 and body 300. Pin 80 may be made of any suitable material and may have any suitable dimensions and configuration. Suitable configurations include those that permit pin 80 to penetrate (with or without an existing incision) human flesh and tissue, in some embodiments, until proximal end 290 reaches and/or accesses the patient's SI joint 30 (see FIG. 13A). In some embodiments, pin 80 is also configured to enter channel 250 of dilator 70 and/or channel 180 of dilator impactor 60. In such embodiments, pin 80 is configured to act as a guide, directing dilator 70 to SI joint 30 or directing dilator impactor 60 to dilator 70. Body 300 may have any suitable configuration, including cylindrical, triangular, oval, rectangular. In some embodiments, proximal end 290 is tip sharp enough to penetrate human flesh and tissue.

FIGS. 7A-F illustrate an embodiment of guide 90. Guide 90 may be made of any suitable material and may have any suitable dimensions and configuration. Suitable configurations guide the surgeon and the tools used by the surgeon to the patient's SI joint in a manner that permits the surgeon to treat the patient's SI joint. In the depicted embodiments, guide 90 has distal end 330, proximal end 340, body 350, stabilizer 360, handle 370, channel 380, tapered region 390, pin guide 380, and dilator access 420. Distal end 330 can be configured to have a flat or substantially flat surface as depicted, or it may have a rounded or other appropriate configuration. In some embodiments, distal end 330 has handle 370, which may be any structure that permits a surgeon to manipulate and/or control guide 90, including inserting it into an incision 940 in a patient 950 (as in, e.g., FIG. 16C). Distal end 330 also includes channel 380, which runs from distal end 330 to proximal end 340. Channel 380 is configured to receive all or part of the body 220 of dilator 70. In some embodiments, channel 380 is configured to receive dilator 70 only when guide 90 is properly oriented relative to the patient's SI joint. In some such embodiments channel 380 is rectangular and body 220 of dilator 70 is rectangular. In other such embodiments, channel 380 may be oval or any other suitable shape and configuration that aids the surgeon in orienting the tools relative to the patient's SI joint. In some such embodiments, body 220 has a first surface 410 which was a width that is greater than that of a second surface 430.

Body 350 of guide 90 may have any suitable configuration. In some embodiments, the dimensions of body 350 are such that body 350 can slide over dilator 70 and into an incision 940 in a patient 950 (as in, e.g., FIG. 16C) and further dilate the incision preferably with minimal tearing or cutting of tissue. In some such embodiments, body 350 is only slightly larger than channel 380. Toward the proximal end 340 of guide 90, is tapered region 390. Tapered region 390 is an area where body 350 narrows. In some embodiments, tapered region 390 reaches its narrowest point at proximal end 340. In some embodiments, tapered region 390 is configured to permit guide 90 to more easily access an incision 940 in a patient 950 (as in, e.g., FIG. 16C) and/or to permit guide 90 to penetrate to the patient's SI joint 30 fitting at least partially between sacrum 10 and ilium 20 (see, e.g., FIG. 16A). In some embodiments, body 350 may also comprise one or more stabilizers 360. Stabilizer 360 can be any structure suitable to stabilize guide 90 while within incision 940 in a patient 950 (as in, e.g., FIG. 16C). In some embodiments, stabilizer 360 is a structure that facilitates attachment of a stabilizing structure to guide 90. For example, stabilizer 360 may have a channel that permits a stabilizing pin 980 to pass through stabilizer 360 and into patient 950 (as in, e.g., FIGS. 17A-B). In some embodiments, body 350 also may comprise dilator access 420. Dilator access 420 may comprise any structure that permits the surgeon to access dilator 70 once it has entered channel 380 of guide 90. In some embodiments, dilator access 420 may be configured such that once guide 90 is in proper position with its proximal end 340 proximal to a patient's SI joint and with dilator 70 in channel 380, a surgeon can access removal structure 230 on dilator 70 (e.g., FIG. 5A) and remove dilator 70 from channel 380, while leaving guide 90 in proper position. (see, e.g., FIG. 18).

Figure 29:
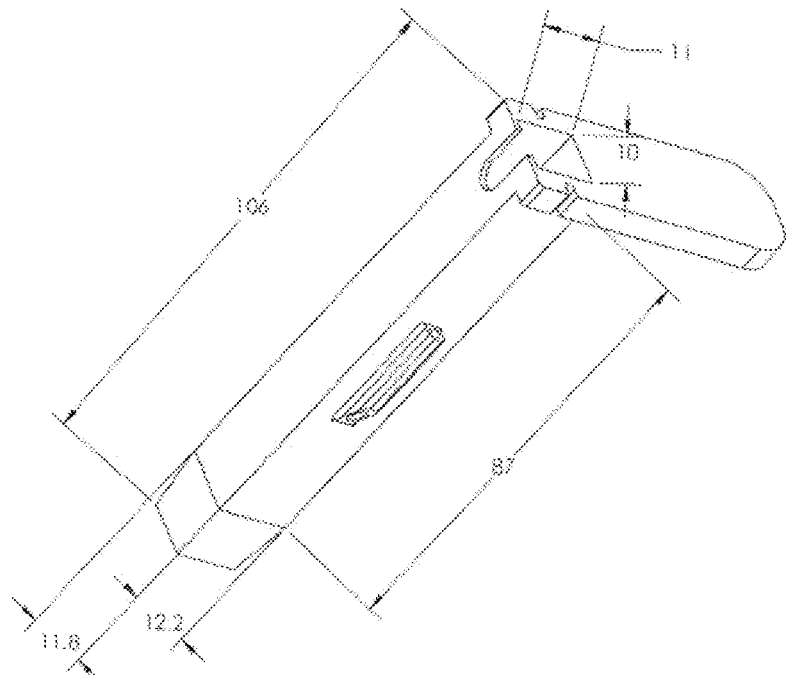
FIG. 29 provides certain relevant dimensions (in mm) in a perspective view of an embodiment of a guide in accordance with the principles of the invention.

Guide 90 may have any suitable dimensions. FIG. 29, shows the dimensions of an embodiment of guide 90, which has a length from distal end 330 to proximal end 340 of about 106 mm, a length from distal end 330 to the beginning of tapered region 390 of about 87 mm, a width of first surface 410 of about 12.2 mm, a width of second surface 430 of about 11.8 mm, a width (parallel to second surface 430) of channel 380 of about 10 mm, and a length (parallel to first surface 410) of channel 380 of about 11 mm. In some embodiments, guide 90 has a length of from about 70 mm to about 140 mm, of from about 85 mm to about 120 mm, or from about 95 to about 110 mm. In some embodiments, guide 90 has a length from distal end 330 to the beginning of tapered region 390 of from about 55 mm to about 120 mm, from about 65 mm to about 100 mm, or from about 75 to about 90 mm. In some embodiments, guide 90 has a width of a first surface 410 of from about 7 mm to about 20 mm, of from about 8 mm to about 15 mm, or from about 10 mm to about 13 mm. In some embodiments, guide 90 has a width of a second surface 430 of from about 6 mm to about 20 mm, of from about 8 mm to about 15 mm, or from about 10 mm to about 13 mm. In some embodiments, channel 380 has a width of from about 5 mm to about 15 mm, of from about 7 mm to about 12 mm, or from about 9 mm to about 11 mm. In some embodiments, channel 380 has a length of from about 5 mm to about 15 mm, of from about 7 mm to about 12 mm, or from about 9 mm to about 11 mm.

FIGS. 8A-D illustrate an embodiment of drill guide 100. Drill guide 100 may have any suitable configuration, dimensions and configuration. In the depicted embodiment, drill guide 100 has distal end 470, proximal end 480, body 490, handle 510, stop 460 and channel 500. Distal end 470 has any suitable configuration and dimensions. In the depicted embodiment, distal end 470 is flat or substantially flat, but it may be rounded or have another configuration. In some embodiments, distal end 470 is typically configured to facilitate a surgeon's application of downward force on drill guide 100. In some embodiments, distal end 470 includes handle 510. In the depicted embodiment, handle 510 is an elongate member extending past both sides of body 490, but handle 510 may be any suitable structure that facilitates the surgeon's manipulation of drill guide 100. In some embodiments, drill guide 100 includes stop 460. In some such embodiments, stop 460 is located proximal to distal end 470. Stop 460 is any structure that interacts with guide 90 in a manner that stops or substantially stops the downward (toward the SI joint) movement of drill guide 100 relative to guide 90. In the depicted embodiment, stop 460 is merely the proximal surface of handle 510, but it may be any suitable structure.

Body 490 of drill guide 100 may have any suitable configuration and dimensions. In some embodiments, body 490 is configured to interact with guide 90 (FIGS. 19A-F) such that it may fit suitably within channel 380 of guide 90. In some such embodiments, body 490 is configured so that it may enter channel 380 of guide 90 in a manner that insures that drill guide 100 is properly oriented with SI joint 30. In some such embodiments body 490 is rectangular having a first surface 520 which has a width that is greater than that of a second surface 530. In some such embodiments, body 490 of drill guide 100 has dimensions substantially similar to the dimensions of body 220 of dilator 70 (e.g., FIG. 5A), though the body 490 of drill guide 100 may have a length that differs from that of body 220 of dilator 70 and may not have a tapered region. In some embodiments, (including the depicted embodiment) the elongate portion of handle 510 is parallel with first surface 520 to further aid alignment.

Drill guide 100 also has a channel 500 that runs from distal end 470 to proximal end 480. In the depicted embodiment, channel 500 is cylindrical, but channel 500 may have any suitable configuration that accommodates a drilling or other tool capable of displacing bone (for example, drill bit 110 (FIG. 9A-B)) and permits such a portion of that tool to pass through channel 500 from distal end 470 to proximal end 480. In such embodiments, channel 500 is configured to permit the use of the drilling tool (e.g., permit a drill bit to rotate at a speed sufficient to displace bone).

Figure 28:
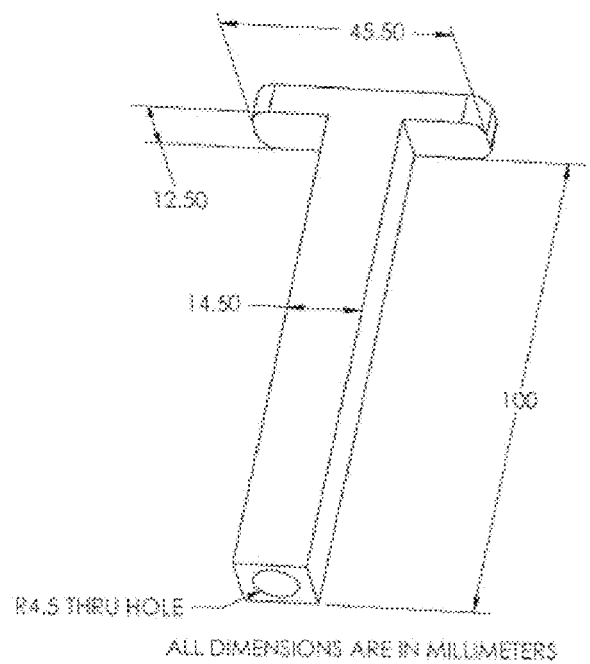
FIG. 28 provides certain relevant dimensions (in mm) in a perspective view of an embodiment of a drill guide in accordance with the principles of the invention.

Drill guide 100 may have any suitable dimensions. FIG. 28 shows an embodiment of drill guide 100 that has a length from stop 460 to proximal end 480 of about 100 mm, a width of first surface 520 of about 14.5 mm, a width of second surface 530 of about 12.5 mm, a length of handle 510 of about 45.5 mm, and a radius of channel 500 of about 4.5 mm. In some embodiments, drill guide 100 has a length of from about 70 mm to about 130 mm, from about 80 mm to about 120 mm, or from about 90 to about 110 mm. In some embodiments, drill guide 100 has a width of a first surface 520 of from about 8 mm to about 25 mm, from about 10 mm to about 20 mm, or from about 12 mm to about 16 mm. In some embodiments, drill guide 100 has a width of a second surface 530 of from about 5 mm to about 25 mm, from about 8 mm to about 20 mm, or from about 10 mm to about 15 mm. In some embodiments, drill guide 100 has a length of handle 510 of from about 10 mm to about 400 mm, from about 25 mm to about 200 mm, from about 35 mm to about 100 mm, or from about 40 mm to about 75 mm. In some embodiments, channel 500 of drill guide 100 has a radius of from about 3 mm to about 10 mm, from about 3.5 mm to about 7 mm, or from about 4 mm to about 5 mm.

FIGS. 9A and 9B illustrate embodiments of drill bit 110. Drill bit 110 may have any suitable configuration that permits it to displace bone and interact with the other tools as described herein. In the depicted embodiments, drill bit 110 has distal end 560, proximal end 570, engagement structure 580, stop 590, body 600, and threaded region 610. Distal end 560 includes engagement structure 580 which is any structure suitable for connecting (directly or indirectly) drill bit 110 to a source of energy. In typical embodiments, engagement structure 580 permits direct interaction with a drill 970 (FIG. 20C). Proximal end 570 is configured to interact with bone and may have any suitable configuration. Proximal end 570 is within threaded region 610. In the depicted embodiment, threaded region 610 is typical threading found in drill bits, but threaded region 610 may be any structure capable of displacing bone. In some embodiments, threaded region 610 is configured to displace bone in a manner that grinds or shaves bone and leaves bone dust, shavings or chips in the void in the patient's SI joint. In such embodiments, the bone dust, shavings or chips would not prevent insertion of graft 40 into the void in the SI joint.

Body 600 of drill bit 110, including threaded region 610, is configured to interact with drill guide 100. Specifically, body 600 is configured to fit within channel 500 of drill guide 100 in a manner that permits drill bit 110 to function (e.g., FIGS. 20A-B). The length of body 600 from stop 590 to proximal end 570 is configured to displace an appropriate amount of bone from the SI joint of a patient by permitting the proximal end 570 of drill bit 110 to extend an appropriate distance into the patient's SI joint and surrounding bones. In some such embodiments, drill bit 110 has a length sufficient to extend a suitable distance past proximal end 340 of guide 90 (FIGS. 7A-D, F) when drill guide 100 is positioned such that stop 460 of drill guide 100 (FIG. 8A-B, D) is in contact with distal end 330 of guide 90 (e.g., FIG. 20B-C). Stop 590 of inserter 130 is any structure that limits the passage of drill bit 110 through drill guide 100. In the depicted embodiment, stop 590 is a ring that extends laterally from body 600 a distance sufficient to contact distal end 470 of drill guide 100 (e.g., FIG. 4A-C) such that drill bit 110 can not proceed any further through channel 500 of drill guide 100 (e.g., FIGS. 20B-C).

Figure 32:
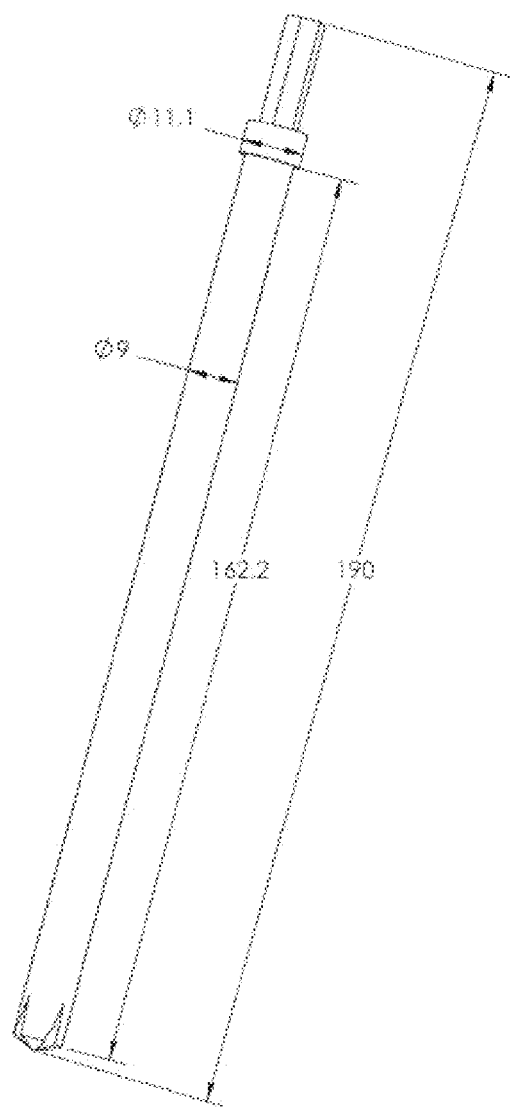
FIG. 32 provides certain relevant dimensions (in mm) in a perspective view of an embodiment of a drill bit in accordance with the principles of the invention.

Drill bit 110 may have any suitable dimensions. FIG. 32 depicts an embodiment of drill guide 110 that has a length from distal end 560 to proximal end 570 of about 190 mm, a length from stop 590 to proximal end 570 of about 162.2 mm, a width of body 600 of about 9 mm, a width of stop 590 of about 11.1 mm. In some embodiments, drill bit 110 has a length of from about 100 mm to about 300 mm, from about 120 mm to about 250 mm, or from about 150 mm to about 200 mm. In some embodiments, drill bit 110 has a length from stop 590 to proximal end 570 of from about 50 mm to about 250 mm, from about 100 mm to about 200 mm, or from about 140 mm to about 175 mm. In some embodiments, drill bit 110 has a width of body 600 of from about 3 mm to about 20 mm, from about 5 mm to about 15 mm, or from about 7.5 mm to about 12.5 mm. In some embodiments, stop 590 has a width of from about 4 mm to about 20 mm, from about 7.5 mm to about 15 mm, or from about 9 mm to about 11 mm.

FIGS. 10A-D illustrate embodiments of broach 120. Broach 120 may have any suitable dimensions and configuration that permit it to enlarge and/or shape a void or hole in bone created by a previous displacement of bone (such as that by drill bit 110). In the depicted embodiments, broach 120 includes distal end 640, proximal end 650, handle 660, stop 720, body 670, and impaction area 680 having serrations 710. Distal end 640 has any suitable configuration and dimensions. In the depicted embodiment, distal end 640 is flat or substantially flat, but it may be rounded or have another configuration. In some embodiments, distal end 640 is typically configured to facilitate a surgeon's application of downward force on broach 120. In some embodiments, distal end 640 includes handle 660. In the depicted embodiment, handle 660 is an elongate member extending past both sides of body 670, but handle 660 may be any suitable structure that facilitates the surgeon's manipulation of broach 120.

Proximal end 650 of broach 120 has any suitable structure and configuration. In the depicted embodiment, proximal end 650 is flat or substantially flat, but it may be rounded or have another configuration. In some embodiments, distal end 650 is configured to facilitate the displacement of bone. Impaction area 680 includes distal end 650. Impaction area 680 can have any configuration suitable to displace bone. In some embodiments impaction area 680 is configured to have substantially the same dimensions as the graft 40 (e.g., FIG. 22D) to be inserted. In such embodiments, impaction area 680 creates a void in the patient's SI joint sufficient to accommodate graft 40. In the depicted embodiments, impaction area 680 includes serrations 710 that facilitate the displacement of bone by broach 120. In other embodiments, impaction area 680 does not include serrations 710. In some embodiments, impaction area 680 is configured to displace bone in a manner that grinds or shaves bone and leaves bone dust, shavings or chips in the void in the patient's SI joint.

In such embodiments, the bone dust, shavings or chips would not prevent insertion of graft 40 into the void in the SI joint.

Figure 21A:
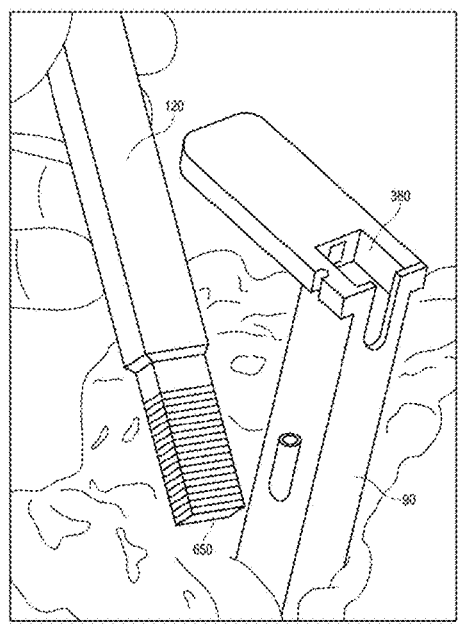
FIG. 21A is an environmental view of a guide and a broach during a procedure in accordance with the principles of the invention.
Figure 21B:
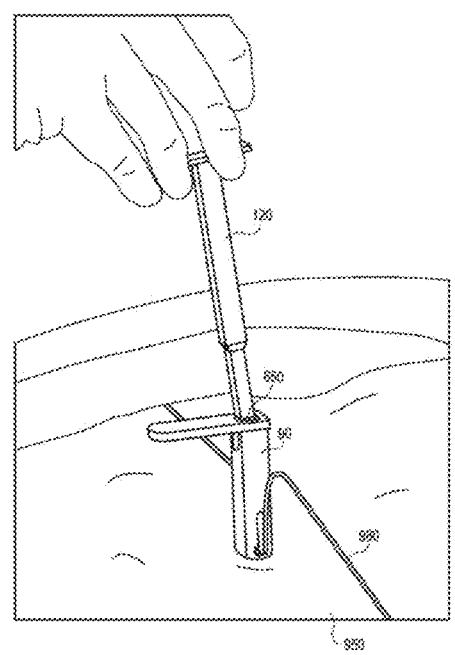
FIG. 21B is another environmental view of a guide and a broach during a procedure in accordance with the principles of the invention.
Figure 21C:
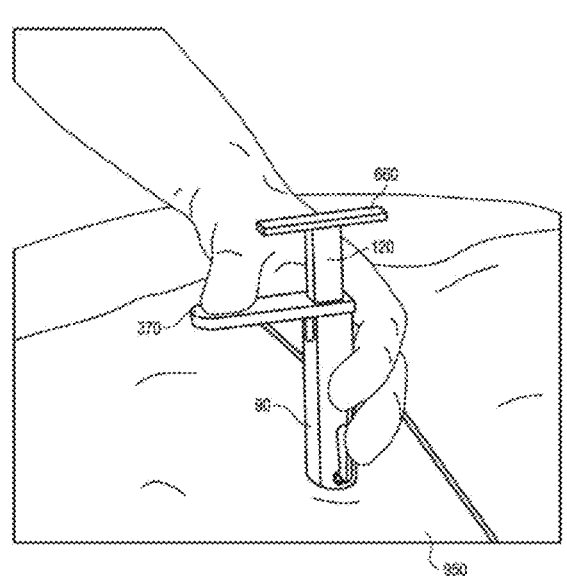
FIG. 21C is another environmental view of a guide and a broach during a procedure in accordance with the principles of the invention.
Figure 21D:
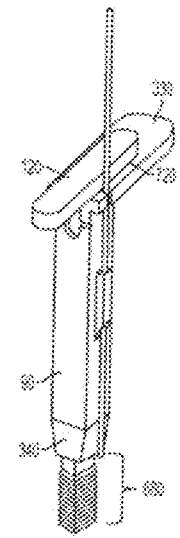
FIG. 21D is a perspective view of a guide and a broach during a procedure in accordance with the principles of the invention.

Body 670 of broach 120 has any suitable dimensions and configuration. In some embodiments, body 670 is configured to interact with guide 90 (FIGS. 21B-D) such that it may fit suitably within channel 380 of guide 90. In some such embodiments, body 670 is configured so that it may enter channel 380 of guide 90 in a manner that insures that broach 120 is properly oriented with SI joint 30. In some such embodiments body 670 is rectangular having a first surface 700 which has a width that is greater than that of a second surface 690. In some such embodiments, body 670 of broach 120 has dimensions substantially similar to the dimensions of body 220 of dilator 70 (e.g., FIG. 5A) and body 490 of drill guide 100. In some such embodiments, the length of broach 120 differs from that of body 220 of dilator 70 and/or body 490 of drill guide 100. In some embodiments, (including the depicted embodiment) the elongate portion of handle 660 is parallel with first surface 700 to further aid alignment.

The length of broach 120 from stop 720 to proximal end 650 is configured to displace an appropriate amount of bone from the SI joint of a patient by permitting the proximal end 650 of broach 120 to extend an appropriate distance into the patient's SI joint and surrounding bones. Stop 720 is any structure that limits the passage of broach 120 through guide 90. In the depicted embodiment, stop 720 is a proximal surface of handle 660 configured to contact distal end 330 of guide 90 (e.g., FIG. 7A-E) such that broach 120 can not proceed any further through channel 380 of guide 90 (e.g., FIG. 21D).

Figure 26:
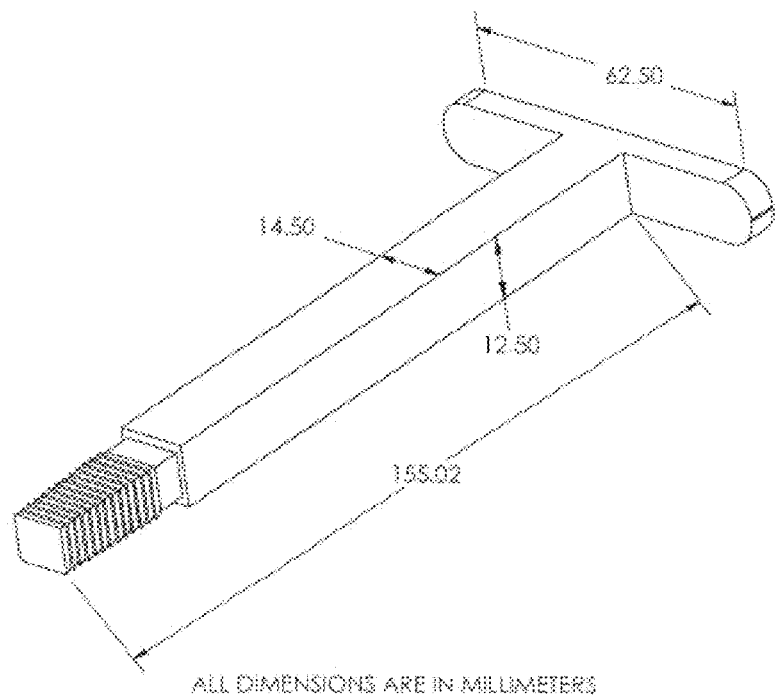
FIG. 26 provides certain relevant dimensions (in mm) in a perspective view of an embodiment of a broach in accordance with the principles of the invention.

Broach 120 may have any suitable dimensions. FIG. 26 illustrates an embodiment having a length from stop 720 to proximal end 650 of about 155.02 mm, a length of handle 660 of about 62.5 mm, a width of first surface 700 of about 14.5 mm, a width of second surface 690 of about 12.5 mm. In some embodiments broach 120 has a length from stop 720 to proximal end 650 of from about 50 mm to about 300 mm, from about 75 mm to about 200 mm, or from about 100 mm to about 175 mm. In some embodiments, handle 660 has a width of from about 10 mm to about 250 mm, from about 35 mm to about 150 mm, or from about 50 mm to about 75 mm. In some embodiments, first surface 700 has a width of from about 5 mm to about 30 mm, from about 10 mm to about 20 mm, or from about 12 mm to about 16 mm. In some embodiments, second surface 690 has a width of from about 4 mm to about 30 mm, from about 7.5 mm to about 20 mm, or from about 10 mm to about 15 mm.

FIGS. 11A-D illustrate embodiments of inserter 130. Inserter 130 may have any suitable dimensions and configuration that permit it to insert a graft 40 (e.g., FIGS. 22A-D) into a void or hole in bone created by a previous displacement of bone (such as that by drill bit 110 and broach 120). In the depicted embodiments, inserter 130 has distal end 740, proximal end 750, stop 760, body 770, channel 780, tapered region 820, and attachment 790. In the depicted embodiment, distal end 740 is flat or substantially flat, but it may be rounded or have another configuration.

Proximal end 750 of inserter 130 includes attachments 790. In the depicted embodiment attachments 790 are fins or extensions, but attachments 790 may be any structure configured to hold a graft 40. In some embodiments, attachments 790 attach and hold graft 40 with force sufficient to retain graft 40 until graft 40 is placed in the void in the patient's SI joint. In some such embodiments, attachments 790 attach and hold graft 40 with force sufficient to retain graft 40 until a downward force is applied to graft 40 (e.g., by the proximal end 860 of impactor 140 (FIGS. 12A-B, D-E)). Attachments 790 are configured to hold graft 40 with sufficient stability, such that during movement of inserter 130, graft 40 is maintained in an orientation appropriate for the placement of graft 40 into the void in the patient's SI joint. Toward the proximal end 750 of inserter 130 is tapered region 820. Tapered region 820 is an area where body 770 narrows. In some embodiments, tapered region 820 reaches its narrowest point at proximal end 750. In some embodiments, tapered region 820 is to permit inserter 130 to penetrate to the patient's SI joint 30 fitting at least partially between sacrum 10 and ilium 20 (see, e.g., FIG. 23B).

Body 770 of inserter 130 has any suitable dimensions and configuration. In some embodiments, body 770 is configured to interact with guide 90 (FIGS. 21B-D) such that it may fit suitably within channel 380 of guide 90. In some such embodiments, body 770 is configured so that it may enter channel 380 of guide 90 in a manner that insures that inserter 130 (and therefore graft 40) is properly oriented with SI joint 30. In some such embodiments body 770 is rectangular having a first surface 800 which has a width that is greater than that of a second surface 810. In some such embodiments, body 770 of inserter 130 has dimensions substantially similar to the dimensions of body 220 of dilator 70 (e.g., FIG. 5A), body 490 of drill guide 100, and body 670 of broach 120. In some such embodiments, the length of inserter 130 differs from that of body 220 of dilator 70 and/or body 490 of drill guide 100 and/or body 670 of broach 120.

Inserter 130 also includes channel 780 which runs from distal end 740 to proximal end 750. In the depicted embodiment channel 780 is rectangular and similar in configuration to body 770. However, channel 780 may have any suitable configuration. In some embodiments, channel 780 is configured to receive an element (e.g., impactor 140 (FIGS. 12A-E)) at distal end 740, wherein the element is configured to extend through channel 780 until the element exits and contacts graft 40 at proximal end 750 with a force sufficient to detach graft 40 from attachments 790.

The length of inserter 130 from stop 760 to proximal end 750 is configured to extend graft 40 an appropriate amount into the void in the patient's SI joint by permitting proximal end 750 and/or graft 40 to extend an appropriate distance into the patient's SI joint and surrounding bones. Stop 760 is any structure that limits the passage of inserter 130 through guide 90. In the depicted embodiment, stop 760 is a rectangular structure that extends laterally from body 770 a distance sufficient to contact distal end 330 of guide 90 (e.g., FIG. 7A-E) such that inserter 130 can not proceed any further through channel 380 of guide 90 (e.g., FIG. 23C).

Figure 31:
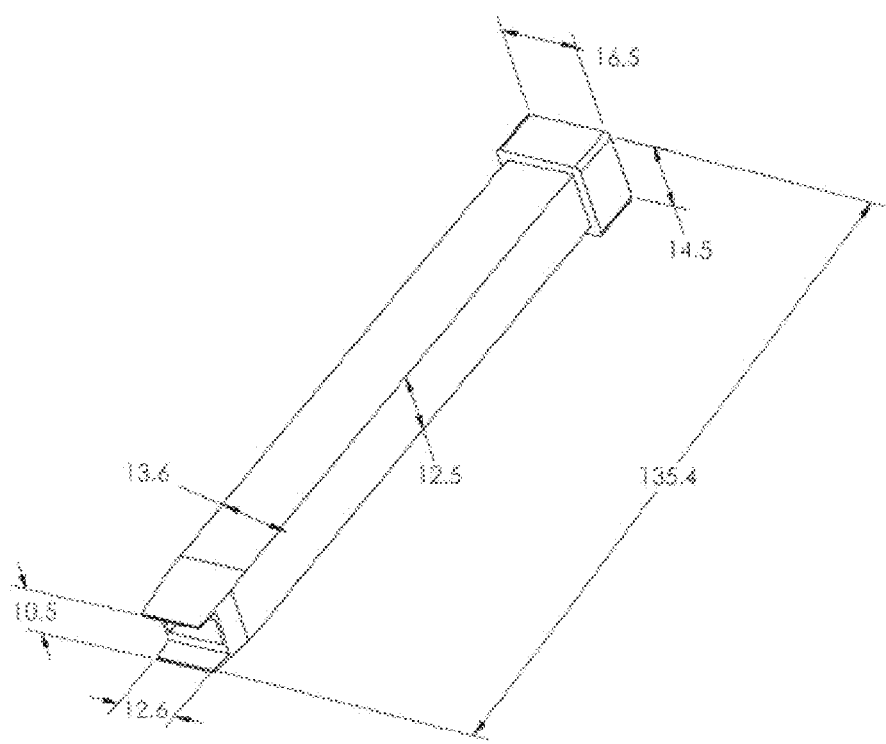
FIG. 31 provides certain relevant dimensions (in mm) in a perspective view of an embodiment of an inserter in accordance with the principles of the invention.

Inserter 130 may have any suitable dimensions. FIG. 31 illustrates an embodiment of inserter 130 having a length from distal end 740 to proximal end 750 of about 135.4 mm, a width of first surface 800 of about 13.6 mm, a width of second surface 810 of about 12.5 mm, a width (parallel to second surface 810) of stop 760 of about 14.5 mm, a length of stop 760 (parallel to first surface 800) of about 16.5 mm, a width (parallel to first surface 800) of attachments 790 of about 12.6 mm, and a distance between attachments 790 of about 10.5 mm. In some embodiments, inserter 130 has a length of from about 50 mm to about 250 mm, from about 100 mm to about 200 mm, or from about 120 mm to about 150 mm. In some embodiments, first surface 800 has a width of from about 4 mm to about 25 mm, from about 10 mm to about 20 mm, or from about 12 mm to about 16 mm. In some embodiments, second surface 810 has a width of from about 3 mm to about 25 mm, from about 7.5 mm to about 20 mm, or from about 10 mm to about 15 mm. In some embodiments, stop 760 has a width of from about 4 mm to about 100 mm, from about 7.5 mm to about 75 mm, or from about 10 mm to about 30 mm. In some embodiments, stop 760 has a length of from about 4 mm to about 100 mm, from about 7.5 mm to about 75 mm, or from about 10 mm to about 35 mm. In some embodiments, attachments 790 have a width of from about 3 mm to about 35 mm, from about 7.5 mm to about 20 mm, or from about 10 mm to about 15 mm. In some embodiments, distance between attachments 790 may be from about 5 mm to about 25 mm, from about 7.5 mm to about 15 mm, or from about 10 mm to about 12 mm.

FIGS. 12A-F illustrate embodiments of impactor 140. Impactor 140 has any suitable configuration and dimensions such that it can extend through channel 780 of inserter 130 until it exits and contacts graft 40 at proximal end 750 of inserter 130 with a force sufficient to detach graft 40 from attachments 790 of inserter 130. In the depicted embodiments, impactor 140 has distal end 850, proximal end 860, body 880, and stop 870. Distal end 850 of impactor 140 is configured to receive force from an outside source. In some embodiments, distal end 850 may have a substantially flattened surface (e.g., as depicted in FIGS. 12B-C) to provide a suitable surface area that may be contacted with a hammer or similar instrument, or to facilitate the application of force by an operator (e.g., a surgeon) of impactor 140.

Figure 24A:
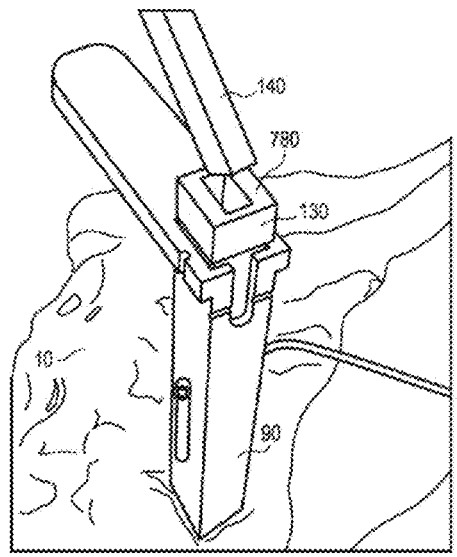
FIG. 24A is an environmental view of a guide, an inserter and an impactor during a procedure in accordance with the principles of the invention.
Figure 24B:
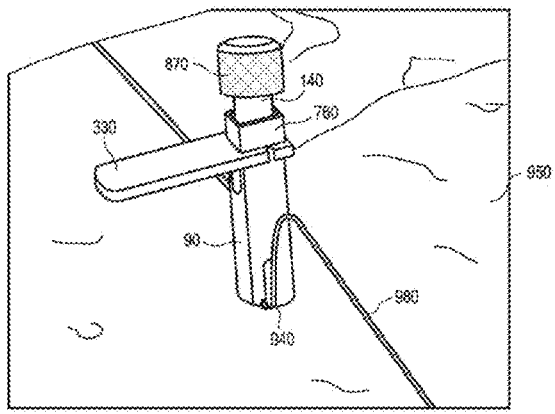
FIG. 24B is another environmental view of a guide, an inserter and an impactor during a procedure in accordance with the principles of the invention.
Figure 24C:
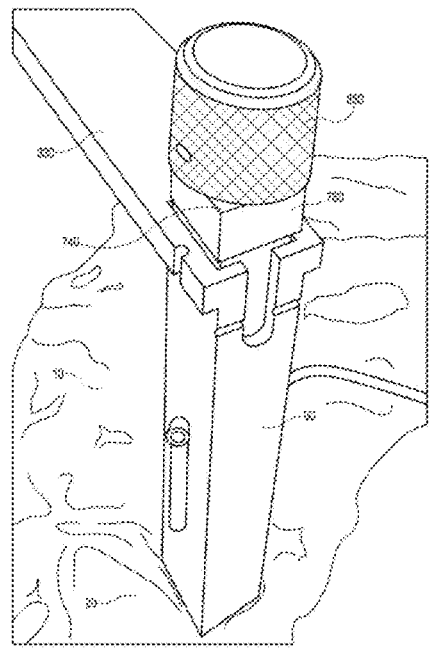
FIG. 24C is another environmental view of a guide, an inserter and an impactor during a procedure in accordance with the principles of the invention.
Figure 24D:
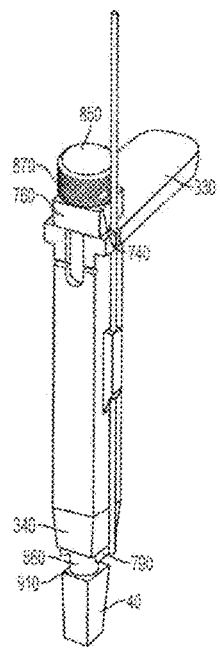
FIG. 24D is a perspective view of a guide, an inserter, a graft and an impactor in accordance with the principles of the invention.

Body 880 may have any suitable configuration and dimensions. In the depicted embodiment, body 880 is rectangular, but it may also be, for example, oval, square, rectangular, triangular, or any other suitable shape or configuration so long as it is compatible with channel 780 of inserter 130 (FIGS. 11B-D). The length of body 880 from stop 870 to proximal end 860 is configured to be sufficient to displace graft 40 from inserter 130 by permitting proximal end 860 to extend an appropriate distance past proximal end 750 of inserter 130. In some such embodiments, impactor 140 has a length sufficient to extend a suitable distance past proximal end 650 of inserter 130 (FIGS. 11A-D) when inserter 130 is positioned such that stop 760 of inserter 130 (FIGS. 11A-D) is in contact with distal end 330 of guide 90 (e.g., FIG. 24C-D).

Proximal end 860 of impactor 140 may have any suitable configuration that permits the transfer of force to graft 40 sufficient to dislodge graft 40 from inserter 130 and into a void in the SI joint of a patient. In some embodiments, proximal end 160 is substantially flat, but other configurations would work as well.

Figure 30:
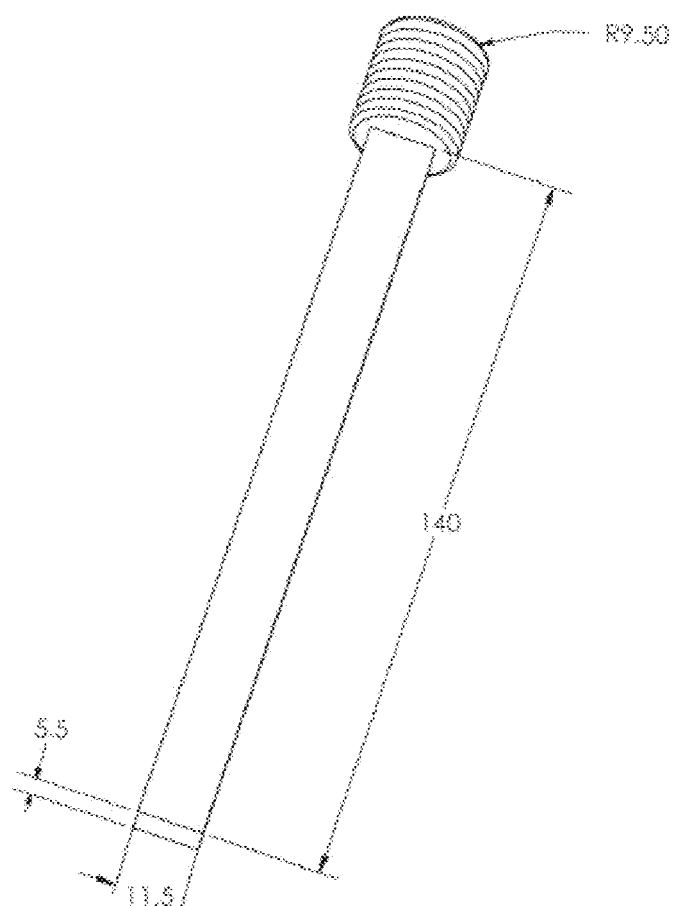
FIG. 30 provides certain relevant dimensions (in mm) in a perspective view of an embodiment of an impactor in accordance with the principles of the invention.

Impactor 140 may have any suitable dimensions. FIG. 30 illustrates an embodiment of impactor 140 having a length from stop 870 to proximal end 860 of about 140 mm, a stop 870 having a radius of about 9.5 mm, a width of first surface 900 of about 11.5 mm, and a width of second surface 890 of about 5.5 mm. In some embodiments, impactor 140 has a length from stop 870 to proximal end 860 of from about 50 mm to about 300 mm, from about 75 mm to about 200 mm, or from about 100 mm to about 175 mm. In some embodiments, stop 870 has a radius of from about 4 mm to about 100 mm, from about 7.5 mm to about 50 mm, or from about 8.5 mm to about 15 mm. In some embodiments, first surface 900 has a width of from about 5 mm to about 40 mm, from about 7.5 mm to about 20 mm, or from about 10 mm to about 15 mm. In some embodiments, second surface 890 has a width of from about 2 mm to about 25 mm, from about 4 mm to about 15 mm, or from about 5 mm to about 10 mm.

The present invention also includes kits that include one or more of the tools as described herein. FIG. 3 illustrates embodiments of tools that may be included in a kit of the present invention. In some such embodiments a kit of the present invention includes one or more of dilator impactor 60, dilator 70, pin 80, guide 90, drill guide 100, drill bit 110, broach 120, inserter 130, and impactor 140. Other surgical kits according to the present invention can include different combinations or subsets of these tools in varying numbers as deemed appropriate for particular needs and uses. The tools may be configured such that they may be used in minimally invasive procedures (e.g., arthroscopic or percutaneous procedures). In some such embodiments, the kit also includes one or more grafts 40. In specific embodiments, the tools are configured to interact with the other tools in a manner that aids the surgeon in keeping a proper orientation with the patient's SI joint, such that graft 40 is properly inserted into the patient's SI joint. In some embodiments, kits include an autoclavable surgical tool kit box, which may be made of any suitable material Methods of the Present Invention In some embodiments, the methods of the present invention substantially fuses the SI joint, such that movement in the joint is minimized or substantially eliminated, thereby diminishing or substantially eliminating the patient's pain and discomfort. The described embodiments treat only one of the patient's SI joints. However, the methods described herein may be used to treat both of the patient's SI joints either at the same or approximately the same time (e.g., during the same procedure) or in sequence.

In some embodiments the method involves numerous steps including, creating an incision proximal to the patient's SI joint, dilating the incision, creating a void in the SI joint, and inserting a graft into the void. Other embodiments include some or all of the following steps, preparing the patient for surgery (e.g., positioning the patient to provide the surgeon access to the SI joint, general or local anesthesia, and the like), locating the SI joint and an incision point for access to the SI joint, insertion of a pin to create an incision, insertion of a dilator over the pin and impacting the dilator to dilate the incision to a width through which instruments may be passed, inserting a guide over the dilator, securing the guide in position, removing the dilator and the guide pin, inserting a drill guide through the guide, inserting a drill bit through the drill guide and using the drill bit to displace bone in the SI joint thereby creating a void, removing the drill bit and drill guide, inserting a broach into the guide and using the broach to enlarge the void in the patient's SI joint, removing the broach from the guide, loading a graft onto an inserter and inserting the graft and inserter into the guide until the graft is positioned proximal to the void in the patient's SI joint, inserting an impactor into the inserter and applying force to displace the graft into the void in the patient's SI joint, removing all instruments, and closing the incision.

Some embodiments include the use of embodiments of the tools or tool kits of the present invention. Other embodiments of the methods of the present invention are performed without using the tools of the present invention. The methods of the present invention may be performed in addition to or in conjunction with one or more of the known methods. Embodiments of the methods of the present invention (and tools of the present invention) are now further described with reference to the Figures. Although the methods are described with respect to the use of certain tools, other tools with different structures may be used and still be within the scope of the present invention.

Figure 13A:
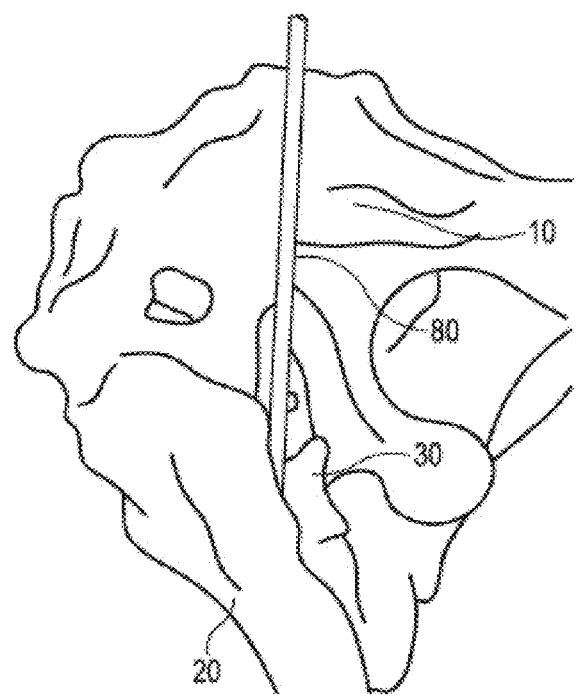
FIG. 13A is a perspective view of a step of a method performed in accordance with the principles of the invention.
Figure 13B:
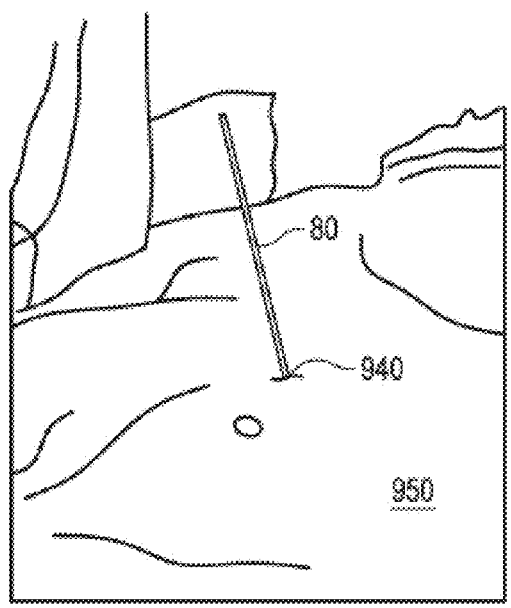
FIG. 13B is a perspective view of another step of a method performed in accordance with the principles of the invention.

FIGS. 13A-B illustrate creation of an incision 940 and insertion of a pin 80 into the patient 950. The incision 940 is preferably made proximal to the patient's SI joint 30, located between sacrum 10 and ilium 20. In this context, proximal means close enough so that a surgeon can operate on and treat the SI joint 30 using minimally invasive techniques. Suitable locations for the incision 940 may be determined by imaging methods (e.g., x-ray), by physiological landmarks on the patient 950, or by any other suitable method. The incision may be made by any suitable method, including scalpel or other cutting or dissection tool, or by a pin 80 that has a proximal end 290 (e.g., FIGS. 6A-B) configured to create an incision. In one embodiment, pin 80 is advanced through the incision 940 and toward the SI joint 30. In some embodiments, pin 80 is (as is shown in FIG. 13A) advanced until its proximal end 290 is in contact with the SI joint 30 or at least partially within SI joint 30. In some embodiments, pin 80 provides a tactile feedback to the surgeon that aids the surgeon's location of SI joint 30. In some embodiments, imaging techniques (e.g., X-ray, fluoroscopy) may be used to locate SI joint 30. In other embodiments, pin 80 is not used and a different instrument is used to locate the SI joint 30 and/or guide other instruments to SI joint 30.

Figure 14A:
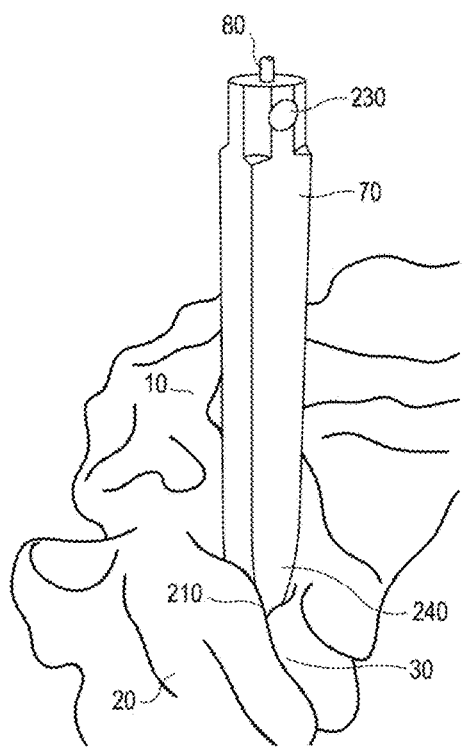
FIG. 14A is an environmental view of a dilator during a procedure performed in accordance with the principles of the invention.
Figure 14B:
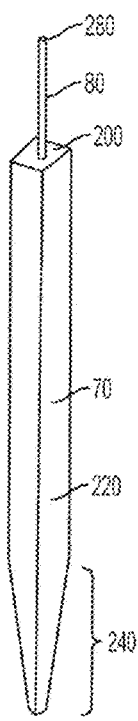
FIG. 14B is a perspective view of a dilator in accordance with the principles of the invention.
Figure 14C:
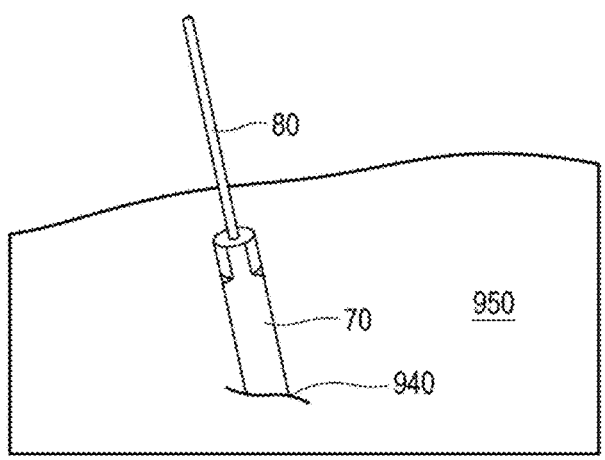
FIG. 14C is another environmental view of a dilator during a procedure in accordance with the principles of the invention.

FIGS. 14A-C illustrate use of dilator 70 to dilate incision 940 in patient 950. In the depicted embodiments, dilator 70 interacts with pin 80 via channel 250 (e.g., FIGS. 5A-E). Pin 80 enters dilator 70 at the dilator's proximal end 210 and dilator 70 is advanced into the patient 950 through incision 940 until proximal end 210 is in contact with the SI joint 30 or at least partially within SI joint 30 (e.g., FIG. 14A). In such embodiments, pin 80 functions to guide the proximal end 210 of dilator 70 to the patient's SI joint 30. In some embodiments, pin 80 is sufficiently long that it extends out of channel 250 at dilator 70's distal end 200. As dilator 70 enters the patient 950 at incision 940, the tapered region 240 pushes the patient's flesh and tissue aside, thereby dilating incision 940 to accommodate body 220 of dilator 70. Preferably, dilator 70 is established in position in an orientation that aids the proper use of other tools to be used in the procedure. For example, in some embodiments body 220 of dilator 70 is rectangular having a first surface 260 which has a width that is greater than a second surface 270 (e.g., FIGS. 5A-E). In such embodiments, dilator 70 is positioned at or in SI joint 30 in a manner that substantially aligns first surface 260 of dilator 70 with the axis along the length of SI joint 30. In other embodiments, other alignment mechanisms may be used.

Figure 15:
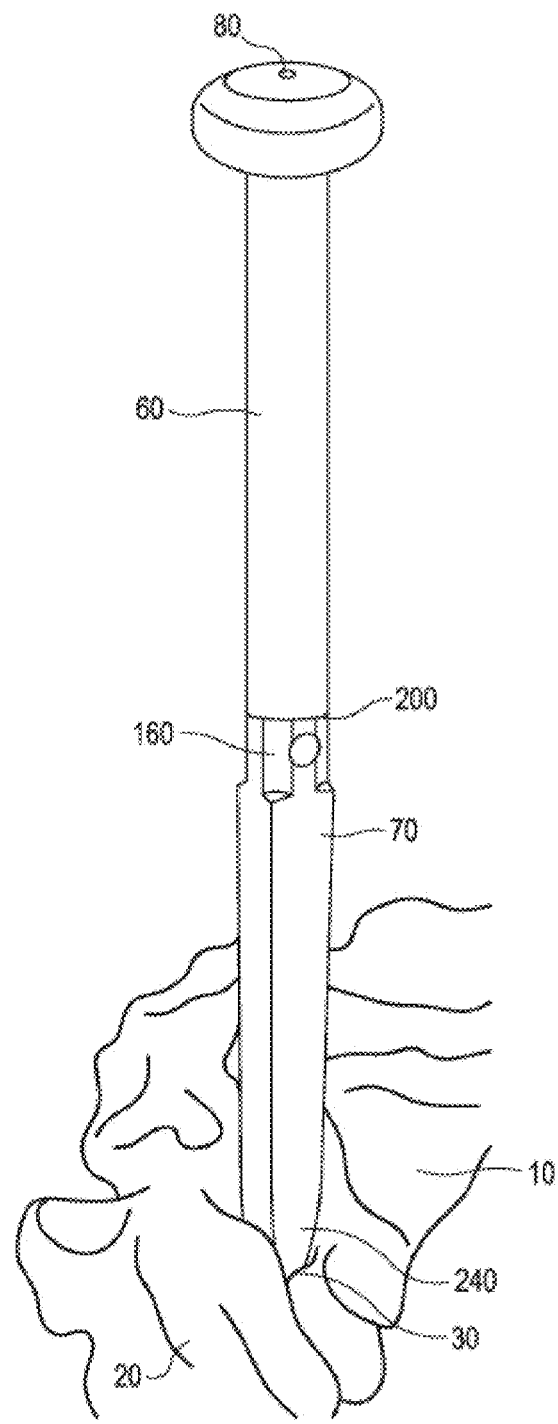
FIG. 15 is a perspective environmental view of a dilator and a dilator impactor during a procedure in accordance with the principles of the invention.

FIG. 15 illustrates the use of dilator impactor 60. In some embodiments dilator 70 is put into proper position using dilator impactor 60. In such embodiments, pin 80 is sufficiently long that it extends out of channel 250 at dilator 70's distal end 200. Dilator impactor 60 is then inserted over pin 80, such that pin 80 enters channel 180 of dilator impactor 60 at proximal end 160. Dilator impactor 60 is advanced over pin 80 until proximal end 160 of dilator impactor contacts distal end 200 of dilator 70. In some embodiments, pin 80 does not extend beyond distal end 150. Once positioned, the surgeon may apply force to the distal end 150 of dilator impactor 60 sufficient to advance dilator 70 into position relative to the patient's SI joint 30.

Figure 16A:
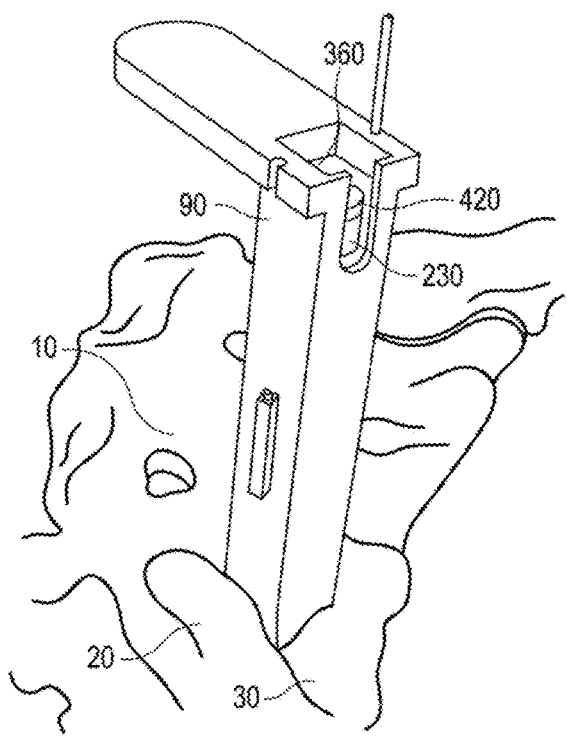
FIG. 16A is an environmental view of a guide during a procedure in accordance with the principles of the invention.
Figure 16B:
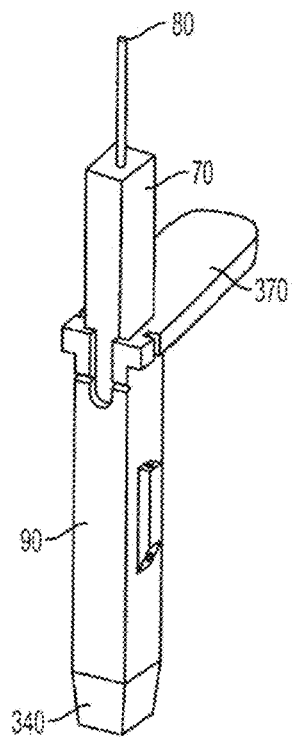
FIG. 16B is a perspective view of a guide and a guide pin during a procedure in accordance with the principles of the invention.
Figure 16C:
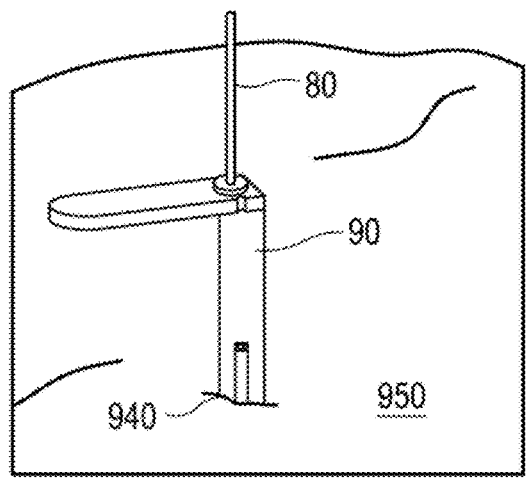
FIG. 16C is an environmental view of a guide and a guide pin during a procedure in accordance with the principles of the invention.

FIGS. 16A-C illustrate use of guide 90. Guide 90 is advanced over dilator 70 and into incision 940 of patient 950. Dilator 70 enters the channel 380 of guide 90 at the distal end 340 of guide 90. In some embodiments, guide 90 may further dilate incision 940. In some such embodiments, tapered region 390 of guide 90 facilitates entry of guide 90 into incision 940. Guide 90 is advanced toward SI joint 30 is advanced into the patient 950 through incision 940 until proximal end 340 is in contact with the SI joint 30 or proximal to the SI joint and in contact with sacrum 10 and/or ilium 20 (e.g., FIG. 16A). In such embodiments, dilator 70 functions to guide the proximal end 340 of guide 90 to the patient's SI joint 30. Preferably, guide 90 is established in position in an orientation that aids the proper use of other tools to be used in the procedure. For example, in some embodiments body 350 of guide 90 is rectangular having a first surface 410 which has a width that is greater than a second surface 430 (e.g., FIGS. 7A-B). In such embodiments, guide 90 is positioned at or near SI joint 30 in a manner that substantially aligns first surface 410 of guide 90 with the axis along the length of SI joint 30. In some such embodiments, handle 370 of guide 90 is also substantially aligned with the axis along the length of SI joint 30. In other embodiments, other alignment mechanisms may be used.

Figure 17A:
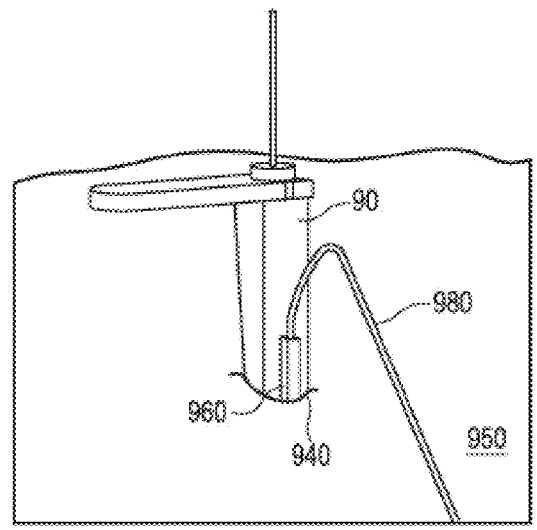
FIG. 17A is an environmental view of a guide and a stabilizing pin during a procedure in accordance with the principles of the invention.
Figure 17C:
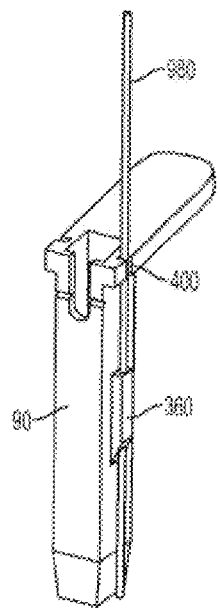
FIG. 17C is an environmental view of a guide and a stabilizing pin during a procedure in accordance with the principles of the invention.
Figure 17B:
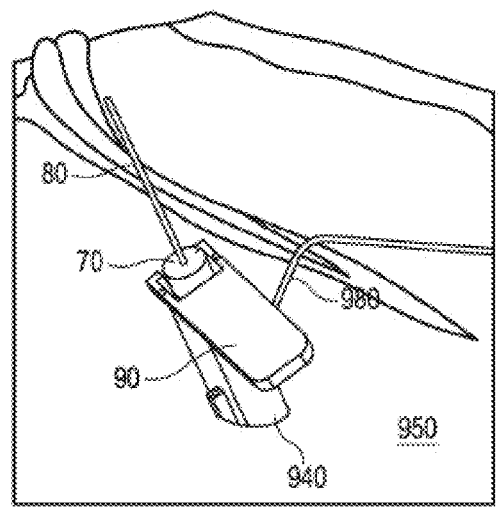
FIG. 17B is a perspective view of a guide and a stabilizing pin during a procedure in accordance with the principles of the invention.

FIGS. 17A-C illustrate an embodiment in which guide 90 is stabilized within incision 940 in patient 950. In the depicted embodiment guide 90 is stabilized using stabilizing pins 980, but any suitable method of stabilizing guide 90 may be used. In some embodiments, the stabilization of guide 90 is such that distal end 340 of guide 90 remains in the proper orientation and in the proper position at or near SI joint 30 throughout the remainder of the procedure. Stabilizing pins 980 may have any suitable structure that permit them to stabilize guide 90. In some embodiments, stabilizing pins 980 have structure substantially similar to that of pin 80 (FIGS. 6A-B). In some embodiments, stabilizing pins 980 can penetrate the skin and/or flesh and tissue of a human. In some embodiments, stabilizing pins 980 may be bent.

FIGS. 17A-C show a stabilizing pin 980 used in conjunction with guide 90. In the depicted embodiments, stabilizing pin 980 goes through a channel in stabilizer 360 of guide 90 and into the patient. In some embodiments, stabilizing pin is aligned with stabilizer 360 of guide 90 using pin guide 400. In some embodiments, stabilizing pin 980 also penetrates into the bone of the patient. As depicted, the portion of stabilizing pin 980 that is outside the patient is at least partially bent to further stabilize guide 90 and also to ensure that stabilizing pin 980 will not interfere with the surgeon's performance of the rest of the procedure. Any suitable number of stabilizing pins 980 may be used to stabilize guide 90.

Figure 18:
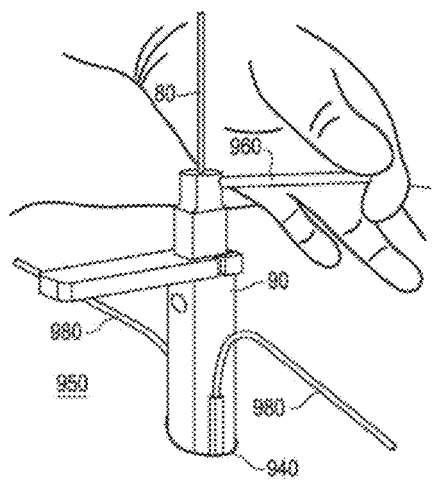
FIG. 18 is an environmental view of a guide and a dilator during a step of a method performed in accordance with the present invention.
Figure 19A:
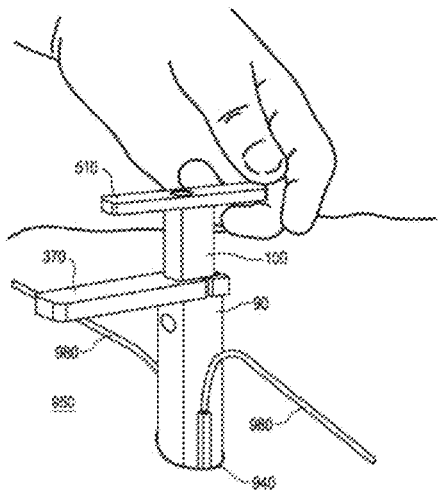
FIG. 19A is an environmental view of a guide and a drill guide during a procedure in accordance with the principles of the invention.
Figure 19B:
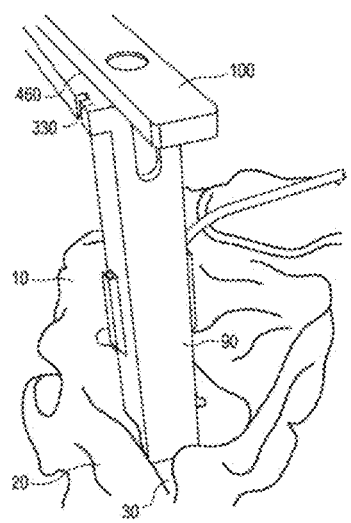
FIG. 19B is another environmental view of a guide and a drill guide during a procedure in accordance with the principles of the invention.
Figure 19C:
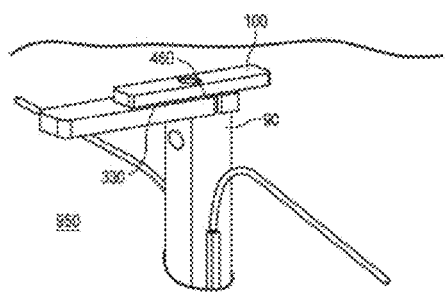
FIG. 19C is another environmental view of a guide and a drill guide during a procedure in accordance with the principles of the invention.
Figure 19D:
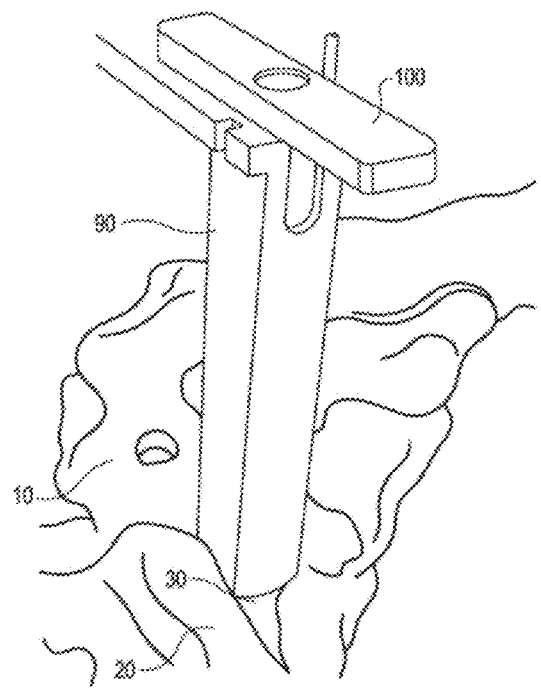
FIG. 19D is another environmental view of a guide and a drill guide during a procedure in accordance with the principles of the invention.
Figure 19E:
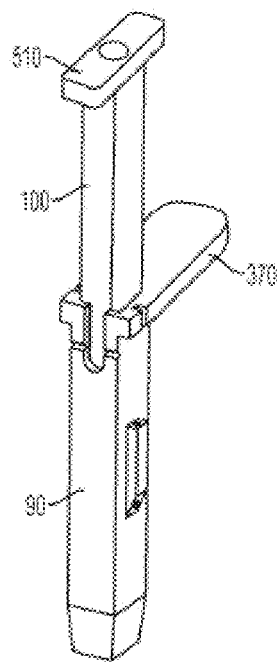
FIG. 19E is a perspective view of a guide and a drill guide during a procedure in accordance with the principles of the invention.
Figure 19F:
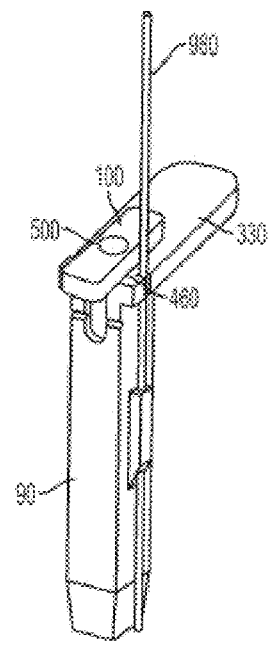
FIG. 19F is another perspective view of a guide and a drill guide during a procedure in accordance with the principles of the invention.

FIG. 18 illustrates an example of the removal of dilator 70 from channel 380 of guide 90. In the depicted embodiment, dilator 70 and guide 90 are oriented relative to each other such that removal structure 230 on dilator 70 (e.g., FIG. 5A) is aligned with access 420 on guide 90 (e.g., FIG. 7B). In the depicted embodiment removal structure 230 interacts with removal tool 960 such that dilator 70 may be removed while leaving guide 90 in its proper position and orientation in incision 940 in patient 950. As illustrated, dilator 70 is removed as it slides away from the patient 950 along pin 80. In some embodiments, pin 80 is removed before dilator 70 is removed; in other embodiments pin 80 is removed after, or at the same time as, dilator 70 is removed from guide 90. As depicted, removal structure 230 is an orifice and removal tool 960 is a rod, but any suitable structures may be used.

FIGS. 19A-F illustrate insertion of drill guide 100 into patient 950 via channel 380 of guide 90. The proximal end 480 of drill guide 100 (e.g., FIGS. 8A-D) enters the channel 380 of guide 90 at the distal end 330 of guide 90 (e.g., FIGS. 7A-F). Drill guide 100 is advanced until stop 460 contacts distal end 330 of guide 90. In some embodiments, when fully inserted into guide 90, the proximal end 480 of drill guide 100 does not extend past the proximal end 340 of guide 90.

Preferably, drill guide 100 is configured such that it will interact with guide 90 only in an orientation that ensures proper positioning of drill guide 100 relative to SI joint 30. For example, in some embodiments body 350 of guide 90 is rectangular having a first surface 410 which has a width that is greater than that of a second surface 430 (e.g., FIGS. 7A-B). In such embodiments, guide 90 is positioned at or ear SI joint 30 in a manner that substantially aligns first surface 410 of guide 90 with the axis along the length of SI joint 30. In some such embodiments, handle 370 of guide 90 is also substantially aligned with the axis along the length of SI joint 30. In the exemplary embodiment, drill guide 100, like guide 90, is rectangular having a first surface 520 which has a width that is greater than that of a second surface 530. In such an embodiment, drill guide 100 will only fit in channel 380 of guide 90 in an orientation that ensures proper orientation of drill guide 100. In some such embodiments, handle 510 of drill guide 100 is aligned with handle 370 of guide 90 when drill guide 100 is in the proper orientation.

Figure 20A:
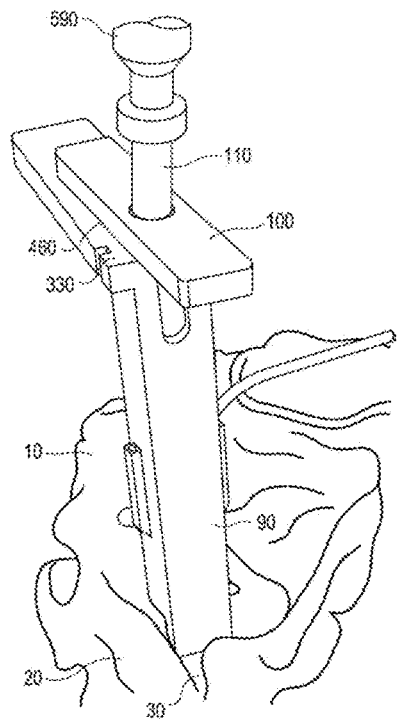
FIG. 20A is an environmental view of a guide, a drill guide and a drill bit during a procedure in accordance with the principles of the invention.
Figure 20B:
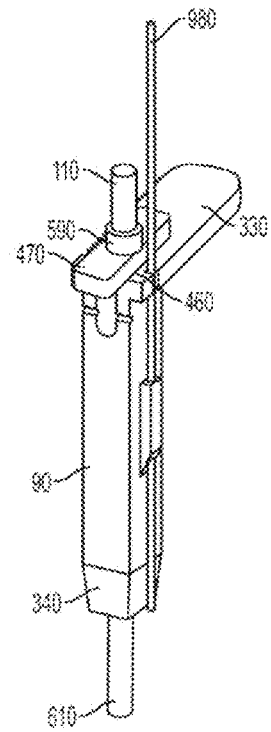
FIG. 20B is a perspective view of a guide, a drill guide and a drill bit during a procedure in accordance with the principles of the invention.
Figure 20C:
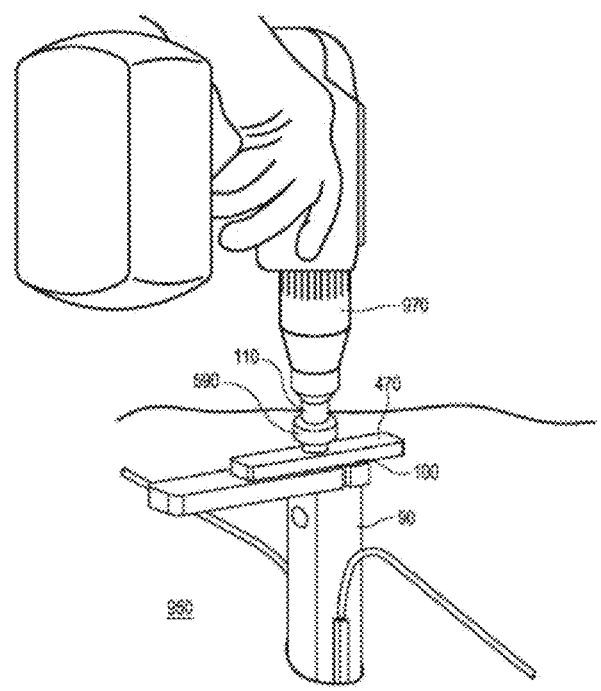
FIG. 20C is an environmental view of a guide, a drill guide, a drill bit and a drill during a procedure in accordance with the principles of the invention.

FIGS. 20A-C illustrate use of an embodiment of a drill bit 110 with guide 90 and drill guide 100. Drill guide 100 is in its proper position with stop 460 in contact with distal surface 330 of guide 90. The proximal end of drill bit 110 is advanced into channel 500 of at the distal end 470 of drill guide 100. Ultimately, drill bit 110 is advanced toward SI joint 30 until stop 590 of drill bit 110 contacts distal end 470 of drill guide 100. Prior to creation of the void in the patient's SI joint 30 drill bit 110 will be positioned such that stop 590 does not contact distal end 470; instead, the proximal end 570 of drill bit 110 is in contact with the patient's SI joint and/or the patients sacrum 10 and/or ilium 20. In some embodiments, drill guide 100, guide 90 and drill bit 110 are configured so when each tool is in its proper position, the proximal end of drill bit 110 makes proper contact with SI joint 30. In some such embodiments, drill bit 110 is positioned so that when activated it will create a void in the patient's SI joint 30 by displacing portions of sacrum 10 and ilium 20. In such embodiments, drill bit 110 is configured such that it will contact the patient's SI joint 30 at a desired portion of the joint and, once activated, will create a void of a desired depth as proximal end 570 will extend a desired distance past proximal end 340 of guide 90.

FIG. 20C illustrates drill 970 operatively attached to drill bit 110. In the depicted embodiment, drill bit 110 is shown fully inserted into drill guide 100 and drill guide 100 is shown fully inserted into guide 90. In preferred embodiments this configuration results in a void in SI joint 30 at the proper position and the proper depth.

FIGS. 21A-D illustrates the use of an embodiment of broach 120. After removal of drill bit 110 and drill guide 100 from guide 90, the proximal end 650 of broach 120 is inserted into channel 380 of guide 90. Broach 120 is inserted until stop 720 contacts distal surface 330 of guide 90. Broach 120 is configured such that when fully inserted, impaction area 680 extends beyond proximal end 340 of guide 90 and into the SI joint 30 of the patient 950. In some embodiments, broach 120 is configured so that impaction area 680 expands the void created by drill bit 110. In other embodiments (e.g., an embodiment wherein drill bit 110 is not used), broach 120 creates a void. In some embodiments, broach 120 is configured such that when fully inserted impaction area 680 will create a void sufficient to receive a graft 40 (e.g., FIG. 22C). Impaction area 680 will have different configurations corresponding, at least roughly, to the desired shape of the graft 40 to be employed in the procedure.

Preferably, broach 120 is configured such that it will interact with guide 90 only in an orientation that ensures proper positioning of broach 120 relative to SI joint 30. Specifically, proper orientation of broach 120 relative to SI joint 30 ensures that broach 120 creates a void in SI joint 30 in a desired orientation such that graft 40 can be inserted into SI joint 30 in a desired orientation. For example, in some embodiments body 350 of guide 90 is rectangular having a first surface 410 which has a width that is greater than that of a second surface 430 (e.g., FIGS. 7A-B). In such embodiments, guide 90 is positioned at or near SI joint 30 in a manner that substantially aligns first surface 410 of guide 90 with the axis along the length of SI joint 30. In some such embodiments, handle 370 of guide 90 is also substantially aligned with the axis along the length of SI joint 30. In the exemplary embodiment, broach 120, like guide 90, is rectangular having a first surface 700 which has a width that is greater than that of a second surface 690. In such an embodiment, broach 120 will only fit in channel 380 of guide 90 in an orientation that ensures proper orientation of broach 120. In some such embodiments, handle 660 of broach 120 is aligned with handle 370 of guide 90 when broach 120 is in the proper orientation.

Figure 22A:
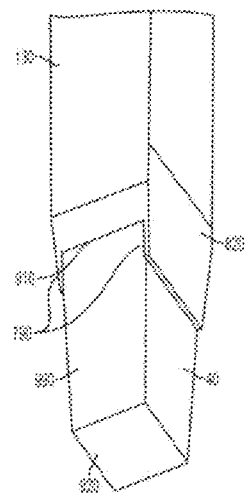
FIG. 22A is a perspective view of an inserter and a graft in accordance with the principles of the invention.
Figure 22B:
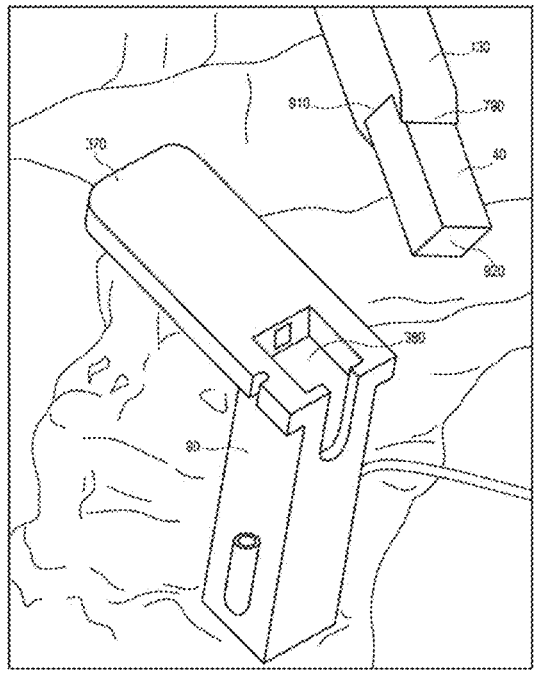
FIG. 22B is an environmental view of a guide, an inserter and a graft during a procedure in accordance with the principles of the invention.
Figure 22C:
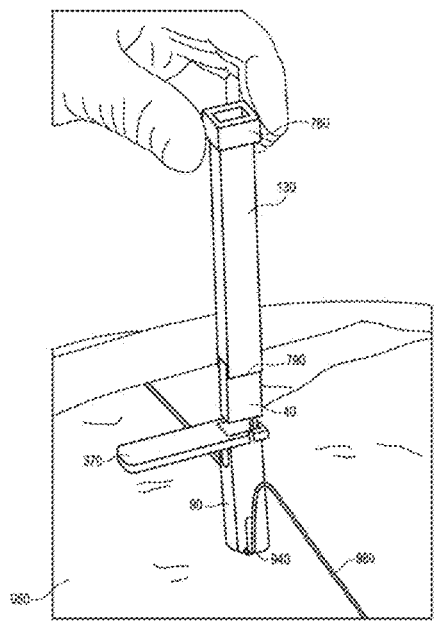
FIG. 22C is another environmental view of a guide, an inserter and a graft during a procedure in accordance with the principles of the invention.

FIGS. 22A-C illustrate the use of an embodiment of inserter 130 to insert a graft 40 into the void in the patient's SI joint 30. Once broach 120 is removed from guide 90, inserter 130 may be inserted into channel 380 of guide 90. Prior to insertion, graft 40 is attached via attachment 790 to the proximal end 750 of inserter 130. In some embodiments, the attachment is sufficiently strong that graft 40 will remain in its orientation and position until a force is applied to its distal end 910.

Figure 23A:
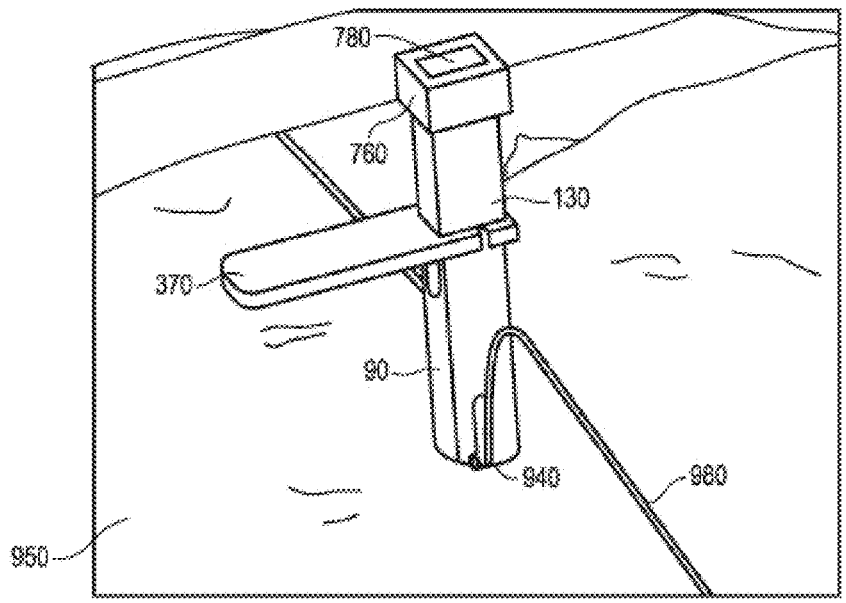
FIG. 23A is an environmental view of an inserter and a guide in accordance with the principles of the invention.
Figure 23B:
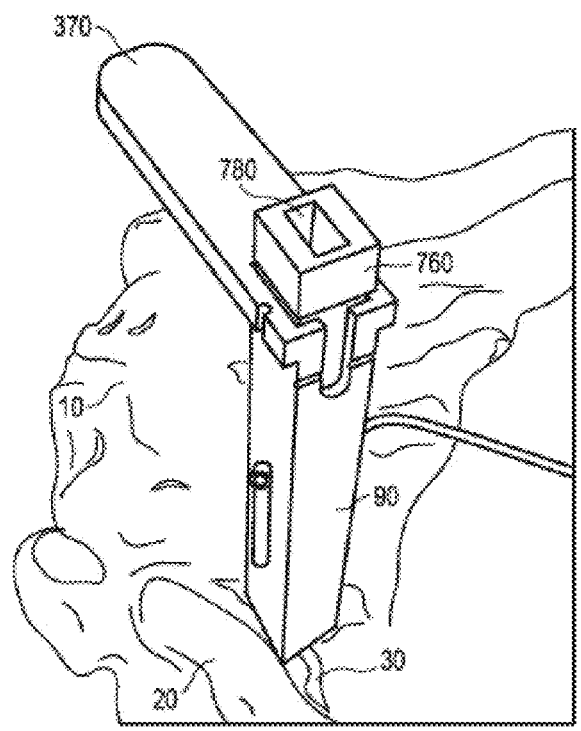
FIG. 23B is another environmental view of an inserter and a guide during a procedure in accordance with the principles of the invention.
Figure 23C:
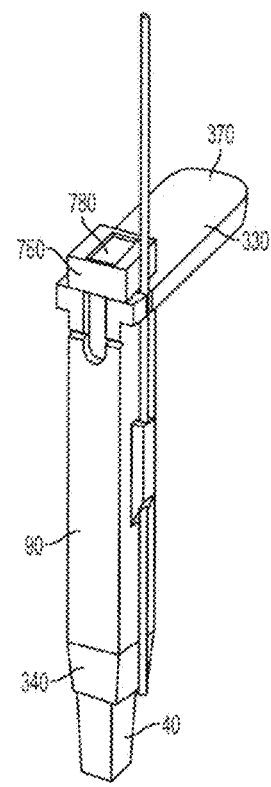

The inserter 130 is then inserted into channel 380 of guide 90, such that proximal end 920 of graft 40 enters channel 380 at the distal end 330 of guide 90 (FIGS. 23A-C). Inserter 130 is advanced toward SI joint 30 until stop 760 contacts distal end 330 of guide 90. When fully inserted, inserter 130 is configured so that graft 40 is oriented for insertion into the void in the patient's SI joint. In some embodiments, when inserter 130 is fully inserted, graft 40 is just above or at least partially in the void in the patient's SI joint 30.

Preferably, inserter 130 is configured such that it will interact with guide 90 only in an orientation that ensures proper positioning of relative to SI joint 30. Specifically, proper orientation of inserter 130 relative to SI joint 30 ensures that inserter 130 is oriented to insert graft 40 in a desired orientation. For example, in some embodiments body 350 of guide 90 is rectangular having a first surface 410 which has a width that is greater than that of a second surface 430 (e.g., FIGS. 7A-B). In such embodiments, guide 90 is positioned at or near SI joint 30 in a manner that substantially aligns first surface 410 of guide 90 with the axis along the length of SI joint 30. In some such embodiments, handle 370 of guide 90 is also substantially aligned with the axis along the length of SI joint 30. In the exemplary embodiment, inserter 130, like guide 90, is rectangular having a first surface 800 which has a width that is greater than that of a second surface 770. In such an embodiment, inserter 130 will only fit in channel 380 of guide 90 in an orientation that ensures proper orientation of inserter 130 and, therefore, graft 40.

Figure 22D:
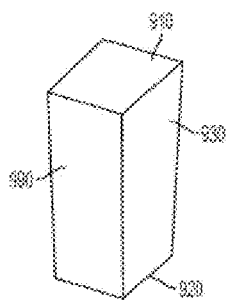
FIG. 22D is a perspective view of a graft in accordance with the principles of the invention.

FIG. 22D illustrates an embodiment of graft 40. Graft 40 may be made of any suitable material and may have any suitable configuration. In the depicted embodiment, graft 40 is substantially rectangular, has a distal end 910, a proximal end 920, a first surface 930 and a second surface 990. In some embodiments, graft 40 is tapered such that first surface 930 and/or second surface 990 decrease in width from distal end 910 to proximal end 920. Preferably, graft 40 is configured such that it will interact with inserter 130 and/or channel 380 of guide 90 only in an orientation that ensures proper positioning of graft 40 relative to SI joint 30. For example, in some embodiments body 350 of guide 90 is rectangular having a first surface 410 which has a width that is greater than that of a second surface 430 (e.g., FIGS. 7A-B). In such embodiments, guide 90 is positioned at or near SI joint 30 in a manner that substantially aligns first surface 410 of guide 90 with the axis along the length of SI joint 30. In the exemplary embodiment, inserter 130, like guide 90, is rectangular having a first surface 800 which has a width that is greater than that of a second surface 770. In such an embodiment, inserter 130 will only fit in channel 380 of guide 90 in an orientation that ensures proper orientation of inserter 130 and, therefore, graft 40. In such embodiments, graft 40 is configured to only attach to inserter 130 in an orientation that insures proper orientation of graft 40 relative to SI joint 30 (e.g., FIG. 22A). In some such embodiments, graft 40 is rectangular, like inserter 130 and guide 90, and has a first surface 930 which has a width that is greater than that of a second surface 990.

Figure 33A:
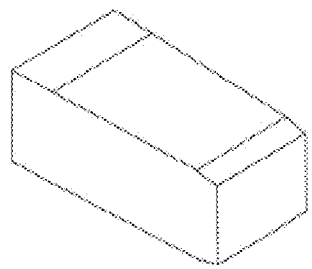
FIG. 33A is a perspective view of an embodiment of a bone graft in accordance with the principles of the invention.
Figure 33B:
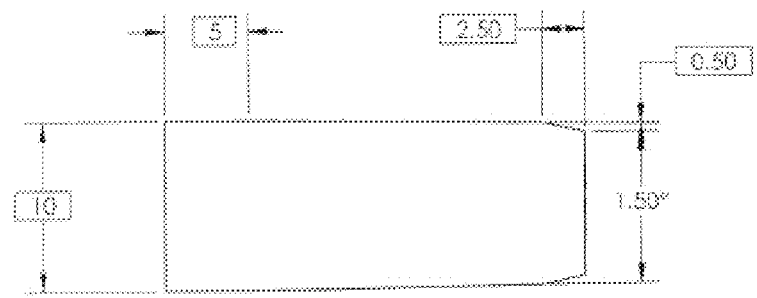
FIG. 33B provides certain relevant dimensions (in mm) in a side elevation view of an embodiment of a bone graft in accordance with the principles of the invention.
Figure 33C:
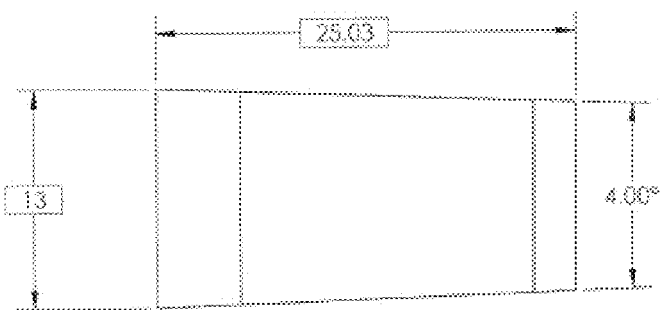
FIG. 33C provides certain relevant dimensions (in mm) in another side elevation view of an embodiment of a bone graft in accordance with the principles of the invention.

Graft 40 may have any suitable dimensions. Suitable dimensions include those that are appropriate given the size of the SI joint 30 and the patient's sacrum 10 and ilium 20. FIGS. 33A-C illustrate a length from distal end 910 to proximal end 920 of about 25.03 mm, a width of first surface 930 of about 13 mm, a width of second surface 990 of about 10 mm, a taper of width of first surface 930 of about 4.0 degrees, a taper of second surface 990 of about 1.5 degrees, a first tapered region of second surface 990 having a length of about 5 mm, and a second tapered region at the proximal end 920 of second surface 990 having a length of about 2.5 mm. In some embodiments, graft 40 has a length of from about 10 mm to about 40 mm, of from about 15 mm to about 30 mm, or from about 20 mm to 27.5 mm. In some embodiments, first surface 930 has a width of from about 5 mm, to about 25 mm, from about 7.5 mm to about 20 mm, or from about 10 mm, to about 15 mm. In some embodiments, second surface 990 has a width of from about 5 mm to about 30 mm, from about 7.5 mm to about 20 mm, or from about 9 mm to about 14 mm. In some embodiments first surface 930 has a taper of from about 0 degrees to about 10 degrees, from about 1 degree to about 7.5 degrees, or from about 3 degrees to about 5 degrees. In some embodiments first surface 930 has multiple tapers (in this context a taper is a distinct gradient of tapering—i.e., a surface having two tapers would have areas having two distinct gradients of taper). In some embodiments, second surface 910 has a taper of from about 0 degrees to about 10 degrees, of from about 0.5 degrees to about 5 degrees, or from about 1 degree to about 2.5 degrees. In some embodiments, second surface 990 has multiple tapers. In some such embodiments second surface 990 has a first taper having a length of from about 1 to 20 mm, from about 2.5 to about 10 mm, or from about 4 mm to about 7.5 mm. In some such embodiments second surface 990 has a second taper having a length from about 0.5 mm to about 10 mm, from about 1 mm to about 5 mm, or from about 2 mm to about 3 mm.

In some embodiments, graft 40 may be rectangular, cylindrical, tapered, triangular, or any suitable configuration. In tapered embodiments, any suitable taper gradient may be used. In some embodiments the taper is a Morse taper. In some embodiments, graft 40 may not be a solitary piece, but rather a collection of numerous pieces (e.g., bone chips) or a paste or similar substance. In preferred embodiments, graft 40 is rectangular and tapered.

In some embodiments graft 40 is composed of bone, synthetic bone, metals or alloys, or any other suitable material. In some embodiments graft 40 is composed of cancellous bone and/or cortical bone. In some embodiments, the graft 40 comprises cortical bone surrounded by cancellous bone on the external surfaces of the graft 40. In other embodiments, graft 40 may comprise fins, serrations, ridges or any other suitable structure on an external surface such as first surface 930 and/or second surface 990.

Returning now to the methods of the present invention, FIGS. 24A-D illustrate use of an embodiment of an impactor 140 with inserter 130 and guide 90. Proximal end 860 of impactor 140 is inserted into channel 780 at distal end 740 of inserter 130. Impactor 140 is inserted into channel 780 of inserter 130 until proximal end 860 of impactor 140 reaches the end of channel 780 at proximal end 750 of inserter 130 and makes contact with distal end 910 of graft 40. Sufficient force is applied (by any suitable method, e.g., directly applied by the surgeon or indirectly through the surgeon's use of a hammer or similar device) to distal end 850 of impactor 140 such that stop 870 contacts the distal end 740 of inserter 130, and therefore, proximal end 860 completely dislodges graft 40 from inserter 130 and places it suitably within the void in the patient's SI joint 30 (e.g., FIG. 24D). Impactor 140 is configured such that when inserter 130 is fully inserted into channel 380 of guide 90, and impactor 140 is completely inserted in channel 780 of inserter 130, impactor 140 has a length sufficient to suitably place graft 40 into the void in the patient's SI joint 30. After graft 40 is inserted in SI joint 30, instruments may be removed and the incision closed.

Figure 25A:
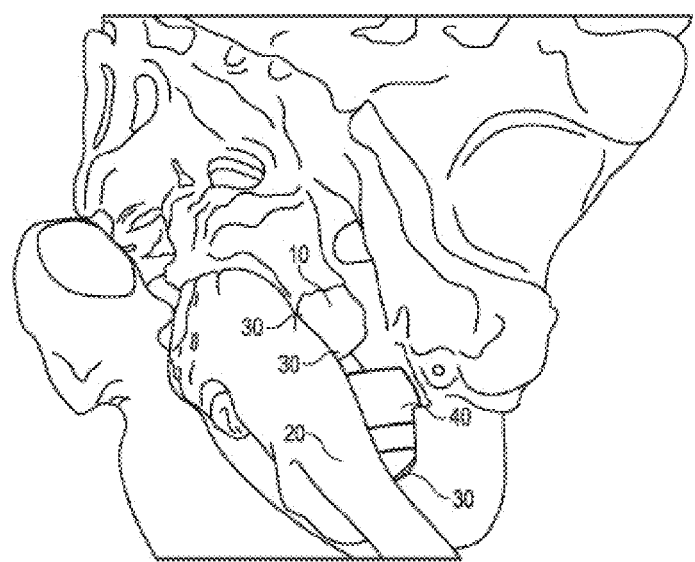
FIG. 25A is an environmental view of a graft implanted in an SI joint in accordance with the principles of the invention.
Figure 25B:
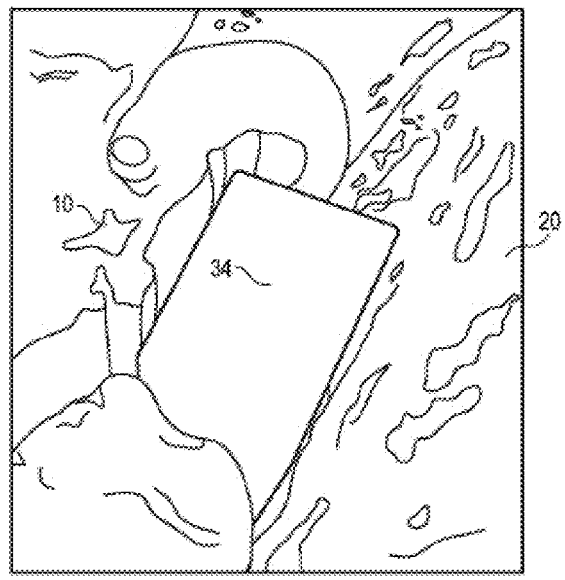
FIG. 25B is an environmental view of a graft implanted in an SI joint in accordance with the principles of the invention.

FIGS. 25A-B show graft 40 properly inserted into the SI joint 30 between sacrum 10 and ilium 20 of the patient. Proper positioning of graft 40 within SI joint 30 may be verified by any suitable method, including various imaging techniques.

Figure 27:
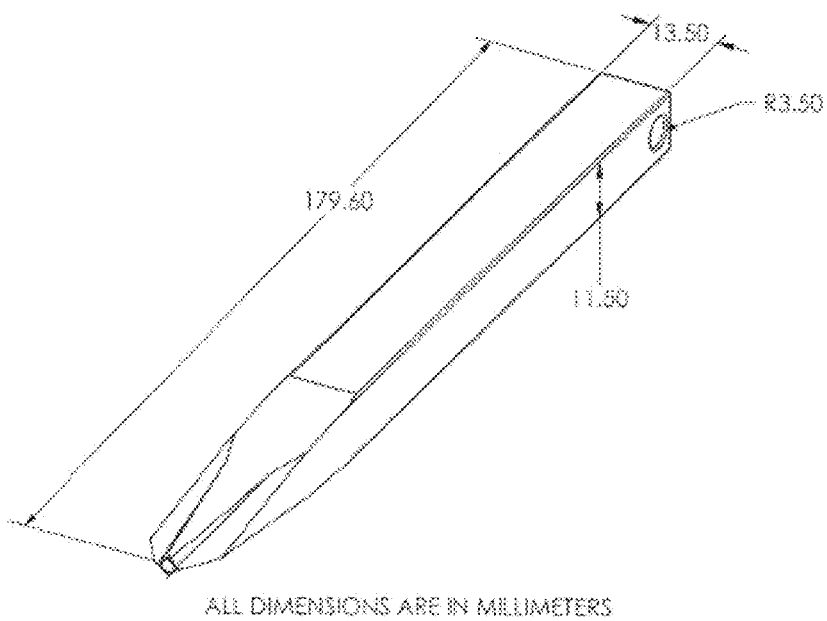
FIG. 27 provides certain relevant dimensions (in mm) in a perspective view of an embodiment of a dilator in accordance with the principles of the invention.

FIGS. 26-33 provide exemplary embodiments of the tools of the present invention. FIG. 26 provides certain relevant dimensions (in mm) in a perspective view of an exemplary broach of the present invention. FIG. 27 provides certain relevant dimensions (in mm) in a perspective view of an exemplary dilator of the present invention. FIG. 28 provides certain relevant dimensions (in mm) in a perspective view of an exemplary drill guide of the present invention. FIG. 29 provides certain relevant dimensions (in mm) in a perspective view of an exemplary guide of the present invention. FIG. 30 provides certain relevant dimensions (in mm) in a perspective view of an exemplary impactor of the present invention. FIG. 31 provides certain relevant dimensions (in mm) in a perspective view of an exemplary inserter of the present invention. FIG. 32 provides certain relevant dimensions (in mm) in a perspective view of an exemplary reamer of the present invention. FIGS. 33A-C provide certain relevant dimensions (in mm) of an exemplary bone graft of the present invention. FIG. 33A provides a side view of an exemplary bone graft of the present invention. FIG. 33B provides a side view of FIG. 33A rotated 90 degrees. FIG. 33C provides a perspective view of the exemplary bone graft of the present invention.

Figure 34A:
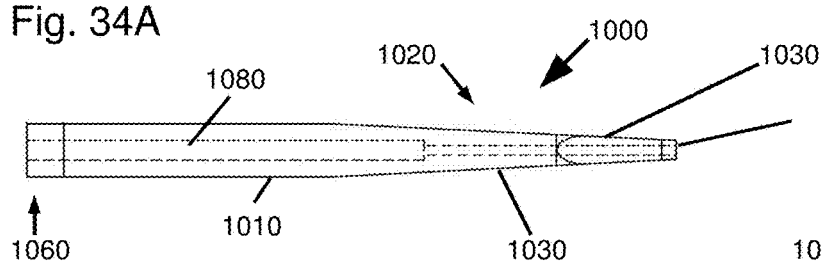
FIG. 34A is a side cross-sectional view of a blunt joint finding instrument in accordance with the principles of the invention.
Figure 34C:
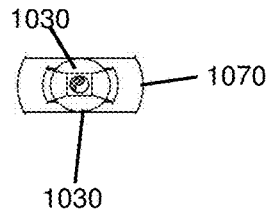
FIG. 34C is a bottom plan view of a blunt joint finding instrument in accordance with the principles of the invention.
Figure 34B:
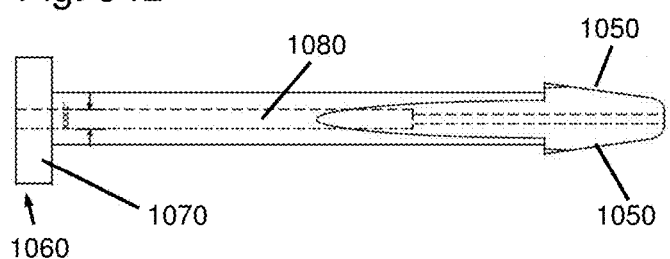
FIG. 34B is another side cross-sectional view of a blunt joint finding instrument in accordance with the principles of the invention.

FIGS. 34A to 34C show a blunt joint finding instrument 1000 in accordance with the principles of the invention. The blunt joint finding instrument 1000 may have an elongate body 1010 having a circular or oval cross-section and a proximal tapered region 1020 where the body 1010 narrows due to opposing planar tapered surfaces 1030 that approach each other along a proximal direction toward the proximal end 1040. The tapered surfaces 1030 of this embodiment have a shovel or spade design the sides 1050 of which taper inward and curve to a flat blunt end at the proximal end 1040.

The distal end 1060 of the body 1010 may include a rectangular handle 1070 that may assist in positioning and manipulating the joint finding instrument 1000. A cylindrical central bore 1080 may extend through the entire length of the body 1010 of the finding instrument 1000 and may be configured to accommodate a guide pin such as guide pin 80 described above.

The curved blunt proximal end 1040 may be inserted into an incision in a patient's and positioned on or near the crest of the ilium. From there, a surgeon may move the blunt joint finding instrument 1000 in the direction of the sacrum until the opening into the sacroiliac joint is identified. Once the opening into the sacroiliac joint has been located, a guide pin such as guide pin 80 may be inserted into the bore 1080 at the distal end 1060 and pushed into the sacroiliac joint itself. This may be accomplished using an impactor or other instruments. Once the guide pin has been inserted through the finding instrument 1000 such that its proximal end has entered the sacroiliac joint, the finding instrument 1000 may be slid in a distal direction out of the patient and off of the guide pin. And incising tool may then be slid over the guide pin to clear away soft tissue and expose the joint and associated bone tissue.

Figure 35A:
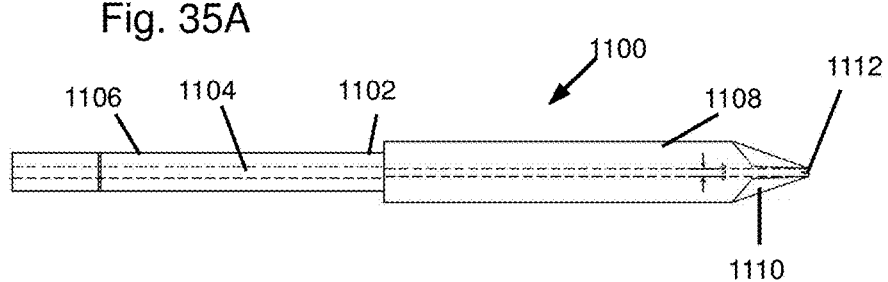
FIG. 35A is a side cross-sectional view of an incising tool in accordance with the principles of the invention.
Figure 35C:
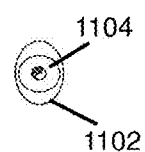
FIG. 35C is a top plan view of an incising tool in accordance with the principles of the invention.
Figure 35B:
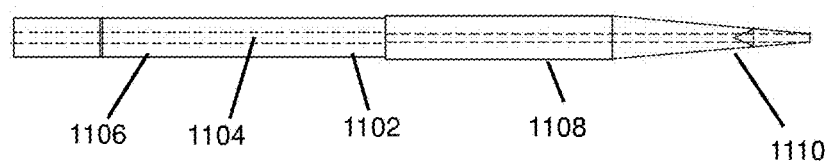
FIG. 35B is another side cross-sectional view of an incising tool in accordance with the principles of the invention.

FIGS. 35A to 35C show and incising tool 1100 that may an elongate body 1102 having a cylindrical internal bore 1104 that may be sized and configured to accommodate a guide pin such as guide pin 80 described above. The elongate body 1102 in this embodiment has a substantially oval or circular cross-section. The distal region 1106 of the incising tool 1100 may be thinner and have less girth than the proximal region 1108. The proximal region 1108 may be thicker and may include a conical tapered region 1110 at the proximal end 1112 of the incising tool 1100. The incising tool 1100 has a similar function to the incisor 70 described above. It may be used for cutting through fascia, ligaments, muscle and any other tissue covering the sacroiliac joint. This may be accomplished using a hammer and optionally and impactor to force the incising tool 1100 through the soft tissue.

Figure 36A:
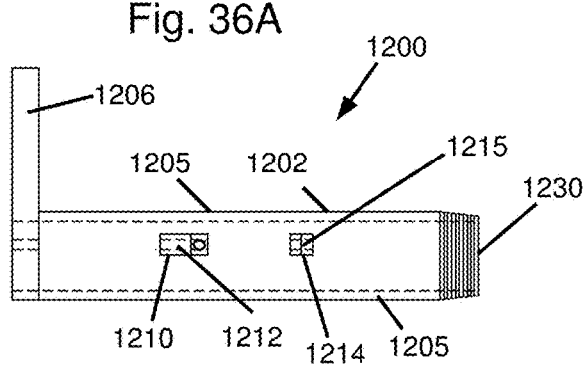
FIG. 36A is a side elevation view of a portal in accordance with the principles of the invention.
Figure 36C:
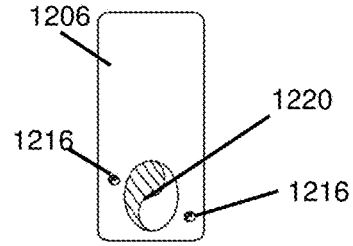
FIG. 36C is a top plan view of a portal in accordance with the principles of the invention.
Figure 36B:
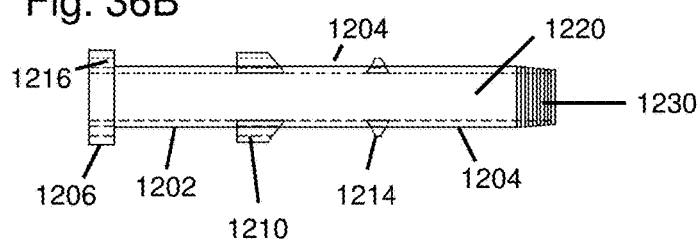
FIG. 36B is another side elevation view of a portal in accordance with the principles of the invention.

FIGS. 36A to 36C show a portal 1200 that is similar to the guide 90 described above. In general, the terms guide and portal may be interchangeably in this description and both generally refer to a device in accordance with the principles of the invention and the description of the guide 90 above and the portal 1200 here. A central portal channel 1220 extends through the entire length of the portal 1200 and has an oval cross-section. Unlike a cannula, the portal 1200 may be held in position using anchoring pins and has a thick, solid body that can withstand substantial force applied to it. In addition to providing access to the sacroiliac joint, it may also support and add stability to other instruments used in conjunction with it.

The portal 1200 in this embodiment has an elongate body 1202 having two sets of opposing sidewalls 1204 and 1205 perpendicular to each other. The elongate body 1202 therefore has an overall shape of a rectangular cuboid. The distal end of the body 1202 includes a rectangular handle 1206 that extends outward on one side and a cantilever fashion and is therefore similar to the handle of the guide 90 above. Generally, the portal handle 1206 will extend in a downward direction relative to the patient, i.e. toward the patient's feet. Also similar to guide 90 above, portal 1200 has two stabilizers 1210 on opposing side surfaces 1204 of the body 1202. Stabilizers 1210 each have a central bore 1212 configured to receive stabilizing pins as described in relation to guide 90 above. Portal 1200 also includes two stabilizing wings 1214 each having a groove for accommodating stabilizing pins inserted through the stabilizers 1210 and into a patient. The handle 1206 also includes two stabilizing bores 1216 through which stabilizing pins are also inserted. Referencing FIG. 36C, it may be seen that the stabilizing bores 1216 are off set from one another. The combination of the stabilizing bores 1216 the stabilizers 1210 and the stabilizing guides 1214 assist in anchoring and securing the portal 1200 securely in place.

In accordance with the principles of the invention, for use with the methods described herein, the portal 1200 is slid over a guide pin and the incising tool 1100 once the incising tool has cut through soft tissue. The proximal end 1230 of the portal 1200 may abut against the ilium and the sacrum at the sacroiliac joint. Once the portal 1200 is positioned, stabilizing pins may be inserted through stabilizing bores 1216, stabilizers 1210 and stabilizing wings 1214. The incising tool 1100 and the guide pin may then be removed through the central channel 1220. The portal 1200 thus provides access to the sacroiliac joint through the portal channel 1220.

Figure 37A:
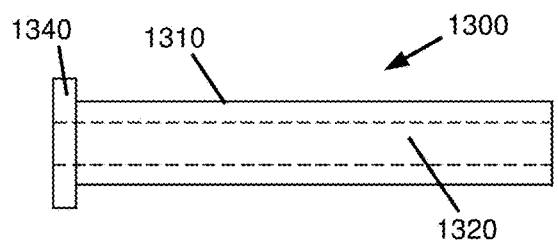
FIG. 37A is a side elevation view of a drill guide in accordance with the principles of the invention.
Figure 37C:
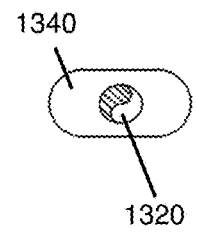
FIG. 37C is a top plan view of a drill guide in accordance with the principles of the invention.
Figure 37B:
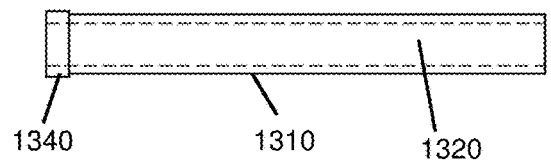
FIG. 37B is another side elevation view of a drill guide in accordance with the principles of the invention.

FIGS. 37A to 37C show a drill guide 1300. Once the portal 1200 has been positioned and stabilized, a drill guide 1300 may be inserted into the portal channel 1220. The drill guide 1300 is similar in design and function to the drill guide 100 described above. However, unlike drill guide 100, drill guide 1300 includes an elongate body 1310 having an oval or circular cross-section configured to fit within the portal channel 1200. The drill guide 1300 includes a drill channel 1320 extending the length of the drill guide. The distal end 1330 of the drill guide 1300 may include a handle 1340. The handle 1340 may be wider than the body 1310 such that when the drill guide 1300 is fully inserted into the portal channel 1220 the drill guide handle 1340 may abut against the portal handle 1206.

FIGS. 38A to 38C show a drill bit 1400. Once the drill guide 1300 is inserted into the portal channel 1220, a drill bit 1400 may be used to drill through the bone surrounding the sacroiliac joint. The drill bit 1400 includes an elongate body 1405 having a distal end 1410 configured to engage with a drill chuck. For example in this embodiment, the distal end 1410 has a hexagonal cross-section similar to those found on other tools configured for insertion into a typical drill chuck. The proximal end 1420 is similar to other working ends of a drill bit, such as for example drillbit 110 described above and is made of material suitable for drilling through bone.

FIGS. 39A to 39C show a small broach 1500 that is similar to broach 120 described above. Broach 120 however has a rectangular body while broach 1500 has an elongate body 1510 having an oval cross-section. The distal end 1530 has a rectangular handle. The proximal end 1520 is tapered and has a series of angled ridges configured to facilitate displacement of bone by applying a back-and-forth motion to the broach 1500. The action of the broach 1500 increases the size of a void created within the sacroiliac joint between the sacrum and the ilium. Once drilling has completed into the sacroiliac joint, the drillbit 1400 and the drill guide 1300 may be removed and the small broach 1500 may be inserted into the portal channel 1220.

FIGS. 40A to 40C show a medium-sized broach 1600. As with the small broach 1500, the medium broach has an elongate body 1610 having an oval cross-section configured to fit within the portal channel 1220. A handle 1630 is located at the distal end of the broach 1600. The proximal end 1640 of the broach is tapered and has a series of ridges similar to that of small broach 1500. If a larger sized void and graft are desired for a particular sacroiliac joint, the medium-sized broach 1600 may be used after applying the small broach.

If an even larger void within the sacroiliac joint is desired, the large broach 1700 shown in FIGS. 41A to 41C may be applied after using the medium broach. The large broach 1700, like the other brooches, includes a handle 1710 at the distal end of an elongate body 1720 having an oval cross-section. The proximal end 1730 is tapered and has a series of ridges or other mechanism for displacing bone and increasing the size of the void created within the sacroiliac joint. What size brooches are required for creating a particular void within a particular sacroiliac joint may depend on a variety of factors. In some instances a small void may be desired while a large void is desired in other situations. When the void has been enlarged to the desired size, an insert may be placed within the void.

FIGS. 42A to 42C show an alternative embodiment of a bone insert 1800 for placement inside a void in a sacroiliac joint. The insert 1800 includes two opposing bone facing sides 1810 and two opposing walls 1820. Two cavities 1830 and 1835 are located between the two opposing walls 1820 and are exposed on each of the two opposing bone facing side 1810. A central beam 1840 extends between the opposing bone facing walls 1810 and separates the cavities 1830 in 1835. Central beam 1840 strengthens the insert 1800 to prevent it from collapsing from the pressure exerted against it by the sacrum and ilium. A central bore 1845 may extend through the beam 1840 and open on the opposing bone facing sides 1810. The central bore 1845 may be configured and sized to engage a screw inserted through the sacrum and ilium to further immobilize the joint. A distal screw hole 1850 has interior threading for engaging and implant inserter 1900 described below.

The insert 1800 may optionally include two or more barbs 1860 extending outward from the inserts and slanted in a distal direction. The barbs 1860 may assist in holding the insert 1800 within a desired location and prevents it from sliding out of the void in the sacroiliac joint into which it is placed. The cavities 1830 in 1835 may include a variety of materials such as stem cells, bone marrow or other materials for facilitating growth of bone through and around the insert, thereby contributing to the immobilization of the sacroiliac joint. The central beam 1840 may optionally include a bore extending between the opposing walls 1820.

FIG. 43 shows an implant inserter 1900 consisting of an elongate body 1910 having a proximal threaded end 1920 configured to screw into the distal screw hole 1850 of the insert 1800. The distal end 1930 is configured to engage a drill chuck and thus has a hexagonal cross-section similar to the distal end of the drillbit 1400. The insert 1800 may be screwed onto the proximal end 1920 of the inserter 1900 and then inserted into a void in the sacroiliac joint through the portal channel 1220. Once inserted into the void, the inserter may be twisted counterclockwise to disengage it from the insert 1800. The barbs 1860 may aid in preventing the insert 1800 from being withdrawn when the inserter 1900 is removed from the portal channel 1220.

After the insert 1800 has been placed within the void, the portal 1220 may be removed and the incision may be sealed according to any of the methods known in the art. The insert 1800 may be comprised of stainless steel or other suitable materials safe for permanent insertion into a person's body. The insert is preferably strong enough to withstand the pressure exerted upon it by the sacrum ilium without collapsing. The insert 1800 shown here has an ovoid shape. Optionally, the insert may have a different shape such as a sphere, a cuboid, a parallelepiped, a hexagonal prism or other configurations. It may be preferable to utilize shapes and designs that improve the inserts strength and integrity.

In addition to the methods described above, it may be desirable to further immobilize and strengthen the sacroiliac joint by inserting one or more screws in a direction perpendicular to the direction from which the insert was placed. Those skilled in the art will appreciate that it is known to apply one or more screws perpendicular to the plane of the sacroiliac joint as a method of immobilizing the joint. It is possible to integrate this known method with the methods described herein.

FIGS. 44A to 44C show a screw alignment guide 2000 for use with the portal 1200 and the other tools described here in. The screw alignment guide 2000 includes a lateral arm 2010 and a parallel arm 2020. The lateral arm 2010, as described below, extends laterally from the portal 1200, outward in the direction of the patient's side, perpendicular to both the portal channel 1220 and the cantilevered portal handle 1206. The parallel arm 2020 extends perpendicularly from the lateral arm and in the same direction as and parallel to the portal channel 1220.

At the distal end 2050 of the parallel arm 2020 is a screw guide 2055 comprised of a circular base 2055 having an annular interior shoulder 2057 encircling a through hole 2052. A stabilizing arm 2060 extends and a proximal direction, that is, toward the patient. The stabilizing arm 2060 is parallel to the lateral arm 2010. A stabilizer 2065 extends perpendicularly from the stabilizing arm 2060 and parallel to the parallel arm 2020, ending in an annular ring 2070 concentric with the circular base 2055 about their axis of radial symmetry 2062. As described in more detail below, the circular base 2055 and concentric annular ring 2070 may be used to guide insertion of a screw into the sacroiliac joint. The proximal end 2012 of the lateral arm 2010 may include a socket 2014 extending in a proximal direction. In this embodiment, the socket 2014 has a hexagonal shape.

FIG. 45 shows the screw alignment guide 2000 having its socket 2014 engaged with the distal end 1930 of the inserter 1900, which is itself still within an extending out of the portal 1200. The lateral arm 2010 of the screw alignment guide 2000 is perpendicular to both the inserter 1900 and the portal handle 1206. The parallel arm 2020 extends in a proximal direction parallel to the portal channel 1220. The parallel arm 2020 extends a predetermined distance such that the axis of radial symmetry 2062 aligns with and passes through the central bore 1845 of the insert 1800 which has been inserted into a void in the sacroiliac joint. Additional components may be utilized to create a starter hole for a screw within the ilium as described below.

Figure 46A:
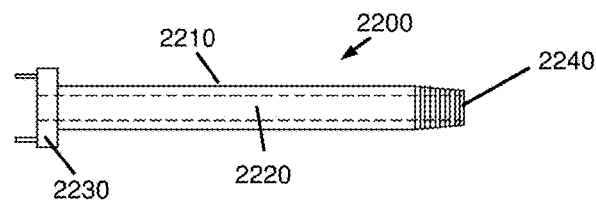
Figure 46C:
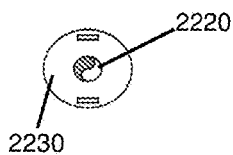
Figure 46B:
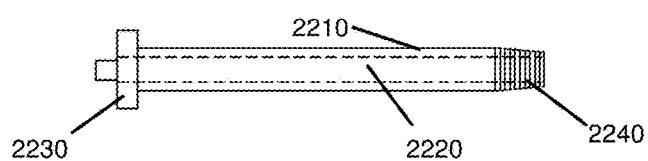

FIGS. 46A to 46C show a screw placement sleeve 2200 in accordance with the principles of the invention. The sleeve 2200 has an elongate body 2210 sized to fit within the openings in the circular base 2055 and the annular ring 2070 of the screw alignment guide 2000. The sleeve 2200 includes a central bore 2220 extending through its entire length. The sleeve 2200 has a handle 2230 at its distal end and a tapered proximal end 2240.

Figure 47A:
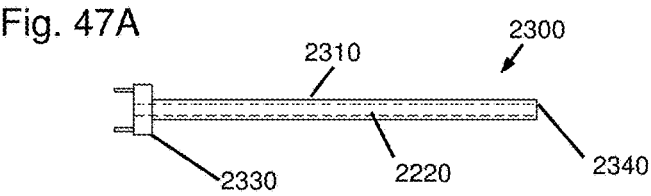
Figure 47C:
Figure 47B:
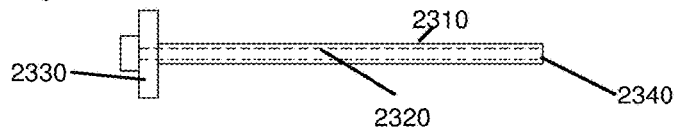

FIGS. 47A to 47C show a screw drill guide 2300 in accordance with principles of the invention. The screw drill guide 2300 in this embodiment includes an elongate body 2310 having a circular cross-section and configured to fit with in bore 2220 of the screw placement sleeve 2200. The elongate body 2310 of the drill guide itself has a central bore 2320 extending from its proximal end 2340 to which handle 2330. The handle 2330 is configured to abut against the handle 2230 of the screw placement sleeve 2200 when the drill guide 2300 is placed inside the bore 2220 of the screw placement sleeve 2200.

Figure 48A:
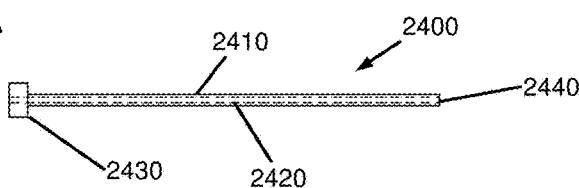
Figure 48C:
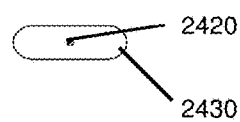
Figure 48B:
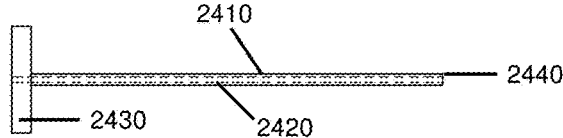

FIGS. 48A to 48C show a pin guide 2400 in accordance with the principles of the invention that may be inserted into the bore 2320 in the drill guide 2300. The pin guide 2400 includes an elongate body 2410 having a central bore 2420 configured to accommodate insertion of a guide pin such as for example guide pin 80 above. The bore 2420 extends from the proximal end 2440 to the handle 2430. The handle 2430 of this embodiment is configured to abut against the handle 2330 of the drill guide 2300 when the body 2410 is fully inserted into the bore 2440. The screw placement sleeve 2200, the drill guide 2300 and the pin guide 2400 are thus configured to slide into one another and may be combined prior to insertion through screw guide 2055.

Figure 49:
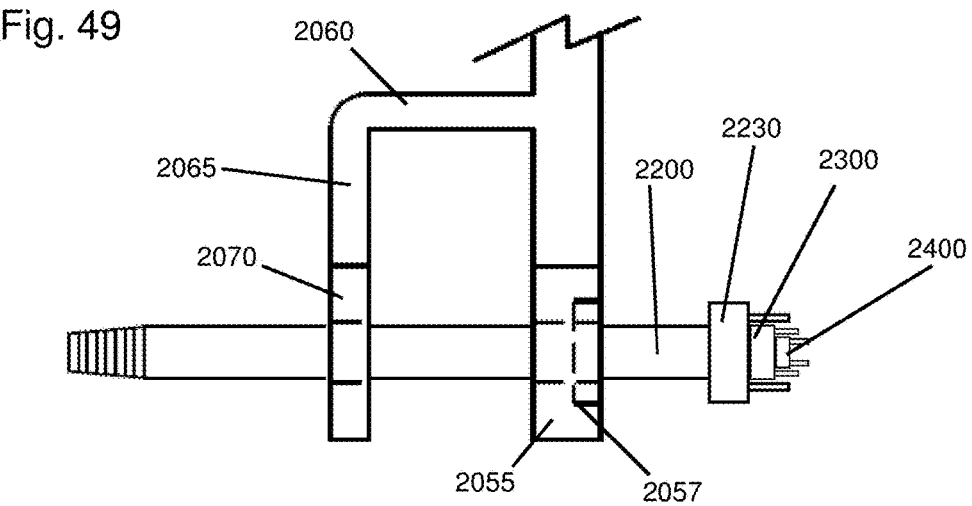

FIG. 49 shows the pin guide 2400 inside the drill guide 2300 which is itself inside the screw placement sleeve 2200. These three devices are then inserted through the screw alignment guide's base 2055 and the annular ring 2070. The handle 2230 of the placement sleeve 2200 abuts against the shoulder 2057 within the circular base 2055. This limits the extent to which the screw placement sleeve 2200 may be inserted through the base 2055 and annular ring 2070. A pin, for example pin 80 above, may be inserted through the pin guide 2400 and the proper distance determined for the placement of a screw next to or through the insert 1800.

Once the proper distance for placement of a screw is determined, the pin guide 2400 may be removed and a drill bit 2500, shown in FIG. 50 may be inserted. The bill drill 2500 includes an elongate body 2510 having a drill bit at its proximal end 5220 and a distal end 2530 configured to engage with a drill Chuck. The drill bit may be affixed to a drill and used to drill a starter hole into the bone perpendicular to the direction in which the insert was placed.

Referring to FIG. 51, once the starter hole has been drilled, the drillbit 2500 and drill guide 2300 may be removed, leaving only the placement sleeve 2200. A screw, for example screw 2600 shown in FIGS. 52A and 52B, may then be inserted into through the ilium and into the sacrum. The screw may be inserted through bore 1845 in the insert 1800. In this manner, the sacroiliac joint is immobilized using an insert 1800 that may supply marrow, stem cells or other bone growing material and also and immobilizing screw.

While specific embodiments of the present invention have been described, other and further modifications and changes may be made without departing from the spirit of the invention. All further and other modifications and changes are included that come within the scope of the invention as set forth in the claims. The disclosures of all publications cited above are expressly incorporated by reference in their entireties to the same extent as if each were incorporated by reference individually.

Whereas, the present invention has been described in relation to the drawings attached hereto, it should be understood that other and further modifications, apart from those shown or suggested herein, may be made within the spirit and scope of this invention. Descriptions of the embodiments shown in the drawings should not be construed as limiting or defining the ordinary and plain meanings of the terms of the claims unless such is explicitly indicated.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The invention claimed is:

1. A method for immobilizing a sacroiliac joint of a patient comprising the steps of:
   creating an incision in a patient's skin proximal and posterior to the patient's sacroiliac joint;
   inserting a blunt joint finding instrument having a curved cross-section, a length defined by a tapered proximal end and a distal end, and a central bore extending from the proximal end to the distal end;
   moving the blunt joint finding instrument until the proximal end abuts the sacroiliac joint of the patient;
   inserting a guide pin into the sacroiliac joint from a posterior direction, wherein a longitudinal axis of the pin lies in a plane defined by the sacroiliac joint;
   removing the blunt joint finding instrument;
   creating a void in the sacroiliac joint, wherein the step of creating the void comprises:
   inserting a graft guide over the guide pin and into the incision;
   securing the graft guide in the incision;
   removing the guide pin;
   inserting a drill guide into the guide;
   inserting a drill bit into the drill guide; and
   attaching a drilling device to the drill bit and drilling the void in the sacroiliac joint;
   removing the drill bit and the drill guide from the guide;
   inserting a broach into the graft guide, wherein the broach has a proximal end and a distal end;
   enlarging the void;
   displacing a portion of the patient's ilium and a portion of the patient's sacrum;
   and inserting a graft into the void in the sacroiliac joint, wherein the step of inserting the graft comprises attaching the graft to an inserter, wherein the inserter has a proximal end and a distal end, wherein the proximal end is configured to attach to the graft, and wherein the inserter comprise a channel running from its distal end to its proximal end;
   inserting the inserter into the graft guide until a stop on the inserter contacts a distal surface of the graft guide; and
   inserting an impactor having a proximal and a distal end into the channel in the inserter until the impactor contacts the graft in the void.

2. The method of claim 1, further comprising a step of dilating the incision prior to inserting the graft guide by placing one or more dilators over the guide pin and removing the dilator prior to inserting the drill guide.

3. The method of claim 1, wherein the step of securing the graft guide in the incision comprises inserting a pin through a portion of the guide and into the patient.

4. The method of claim 1 wherein the graft comprises:
   two opposing bone facing sides, and
   a central bore extending between the two bone facing sides.

5. The method of claim 4 wherein the graft further comprises two opposing walls, each defined by a distal end and a proximal end.

6. The method of claim 4 wherein the graft further comprises a screw hole at the distal end configured to attach to the inserter.

7. The method of claim 4 wherein the graft further comprises a barb on each of the two opposing bone facing sides at the proximal end and extending in a distal direction.

8. A method for immobilizing a sacroiliac joint of a patient comprising comprising the steps of:

creating an incision in a patient's skin proximal and posterior to the patient's sacroiliac joint;

inserting a blunt joint finding instrument having a curved cross-section, a length defined by a tapered proximal end and a distal end, and a central bore extending from the proximal end to the distal end;

moving the blunt joint finding instrument until the proximal end abuts the sacroiliac joint of the patient inserting a guide pin into the sacroiliac joint from a posterior direction, wherein a longitudinal axis of the pin lies in a plane defined by the sacroiliac joint;

removing the blunt joint finding instrument;

creating a void in the sacroiliac joint, wherein the step of creating the void comprises:

inserting a graft guide over the guide pin and into the incision;

securing the graft guide in the incision;

removing the guide pin;

inserting a drill guide into the guide;

inserting a drill bit into the drill guide; and attaching a drilling device to the drill bit and drilling the void in the sacroiliac joint; removing the drill bit and the drill guide from the guide;

inserting a broach into the graft guide, wherein the broach has a proximal end and a distal end;

enlarging the void;

displacing a portion of the patient's ilium and a portion of the patient's sacrum;

and inserting a graft into the void in the sacroiliac joint, wherein the graft comprises two opposing bone facing sides, a central bore extending between the two bone facing sides, two opposing walls, each defined by a distal end and a proximal end, and two chambers defined by the two opposing walls, the two bone facing sides and a central beam extending between the two bone facing walls, wherein the central bore extends through the central beam and extends between the two bone facing sides.

9. A method for immobilizing a sacroiliac joint of a patient comprising comprising the steps of:

creating an incision in a patient's skin proximal and posterior to the patient's sacroiliac joint;

inserting a blunt joint finding instrument having a curved cross-section, a length defined by a tapered proximal end and a distal end, and a central bore extending from the proximal end to the distal end;

moving the blunt joint finding instrument until the proximal end abuts a the sacroiliac joint of the patient;

inserting a guide pin into the sacroiliac joint from a posterior direction, wherein a longitudinal axis of the pin lies in a plane defined by the sacroiliac joint;

removing the blunt joint finding instrument;

creating a void in the sacroiliac joint, wherein the step of creating the void comprises:

inserting a graft guide over the guide pin and into the incision;

securing the graft guide in the incision;

removing the guide pin;

inserting a drill guide into the guide;

inserting a drill bit into the drill guide; and attaching a drilling device to the drill bit and drilling the void in the sacroiliac joint;

removing the drill bit and the drill guide from the guide;

inserting a broach into the graft guide, wherein the broach has a proximal end and a distal end;

enlarging the void;

displacing a portion of the patient's ilium and a portion of the patient's sacrum;

and inserting a graft into the void in the sacroiliac joint, wherein the graft comprises two opposing bone facing sides and a central bore extending between the two bone facing sides;

affixing a screw alignment guide to a distal end of the graft guide, the screw alignment guide comprising a lateral arm extending in a lateral direction, a parallel arm perpendicular to the lateral arm and parallel to the graft guide, and an aperture at a distal end of the parallel arm and aligned with the central bore of the graft;

aligning the screw with the aperture; and inserting the screw into the aperture, through the ilium and into the central bore of the graft.

* * * * *